(12) United States Patent
Green et al.

(10) Patent No.: US 6,673,828 B1
(45) Date of Patent: Jan. 6, 2004

(54) ANALOGS OF 2-PHTHALIMIDINOGLUTARIC ACID

(75) Inventors: Shawn J. Green, Vienna, VA (US);
Glenn M. Swartz, Jr., Jessup, MD (US); Jamshed H. Shah, Columbia, MD (US); John Madsen, Knoxville, MD (US); Adonia E. Papathanassiu, Silver Spring, MD (US); William Fogler, Rockville, MD (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/309,464

(22) Filed: May 11, 1999

Related U.S. Application Data

(60) Provisional application No. 60/085,037, filed on May 11, 1998, provisional application No. 60/097,384, filed on Aug. 21, 1998, and provisional application No. 60/108,037, filed on Nov. 12, 1998.

(51) Int. Cl.$^7$ .................. A61K 31/4035; C07D 209/46
(52) U.S. Cl. ........................................ 514/416; 548/472
(58) Field of Search ........................... 514/416; 548/472

(56) References Cited

U.S. PATENT DOCUMENTS

| | | | |
|---|---|---|---|
| 2,830,991 A | 4/1958 | Keller et al. ................ | 260/281 |
| 3,560,495 A | 2/1971 | Frankus .................... | 260/247.1 |
| 3,563,986 A | 2/1971 | Frankus .................... | 260/247.1 |
| 3,625,946 A | 12/1971 | Heinrich et al. ............ | 260/281 |
| 3,705,162 A | 12/1972 | Graudums et al. .......... | 260/281 |
| 4,552,888 A | 11/1985 | Koppel et al. .............. | 514/474 |
| 4,994,443 A | 2/1991 | Folkman et al. ............. | 514/56 |
| 5,001,116 A | 3/1991 | Folkman et al. ............. | 514/56 |
| 5,021,404 A | 6/1991 | Folkman et al. ............. | 514/26 |
| 5,134,127 A | 7/1992 | Stella et al. ................. | 514/58 |
| 5,385,901 A | 1/1995 | Kaplan et al. ........... | 514/231.5 |
| 5,399,363 A | 3/1995 | Liversidge et al. ......... | 424/490 |
| 5,405,855 A | 4/1995 | Andrulis, Jr. .............. | 514/323 |
| 5,434,170 A | 7/1995 | Andrulis, Jr. .............. | 514/323 |
| 5,443,824 A | 8/1995 | Piacquadio .............. | 424/78.02 |
| 5,502,066 A | 3/1996 | Heinemann ................ | 514/360 |
| 5,605,684 A | 2/1997 | Piacquadio ............. | 424/78.02 |
| 5,605,914 A | 2/1997 | Muller ...................... | 514/339 |
| 5,629,327 A * | 5/1997 | D'Amato .................... | 514/323 |
| 5,643,915 A | 7/1997 | Andrulis, Jr. et al. ....... | 514/279 |
| 5,654,312 A | 8/1997 | Andrulis, Jr. et al. ....... | 514/279 |
| 5,679,696 A | 10/1997 | Fenton et al. ............... | 514/354 |
| 5,731,325 A | 3/1998 | Andrulis, Jr. et al. ....... | 514/323 |
| 5,919,790 A * | 7/1999 | Allen et al. ................ | 514/278 |
| 6,020,358 A * | 2/2000 | Mullet et al. ............... | 514/411 |

FOREIGN PATENT DOCUMENTS

| | | |
|---|---|---|
| AT | 1182709 | 3/1970 |
| EP | 0325199 | 7/1989 |
| EP | 0357061 | 3/1990 |
| EP | 0 688 771 A1 | 6/1995 |
| JP | 58-131978 | 8/1983 |
| JP | 63-119500 | 5/1988 |
| WO | WO 91/10424 | 7/1991 |
| WO | WO 92/14455 | 9/1992 |
| WO | WO 92/18496 | 10/1992 |
| WO | WO 94/20085 | 9/1994 |
| WO | WO 95/04533 | 2/1995 |

OTHER PUBLICATIONS

Klug, et al., "Embryotoxic Effects of Thalidomide Derivatives in the Non–Human Primate Callithrix Jacchus", *Arch. Toxicol.*, vol. 68, pp. 203–205 (1994).

Algire, G. H., "Vascular Reactions of Normal and Malignant tissues In Vivo. I. Vascular Reactions of Mice to Wounds and to Normal and Neoplastic Transplants", *J. Nat'l Canc. Inst.*, pp. 73–85 (1945).

Allegri, A., "Confermata l'inefficacia della Talidomide Nella Terapia dei Tumori", *Gazzetta Medica Italiana*, pp. 124–127 (1964).

Ambs, S. et al., "Interactive Effects of Nitric Oxide and the p53 Tumor Suppressor Gene in Carcinogenesis and Tumor Progression", *The FASEB Journal*, vol. 11, pp. 443–448 (1997).

Apt, W. "Effect of Thalidomide on the Course of Experimental Chagas' Disease", *BOI. Chil. Parasitol*, vol. 20, No. 3, pp. 84–86 (1965).

Aronson, et al., "Thalidomide–Induced Peripheral Neuropathy. Effect of Serum Factor on Nerve Cultures", *Arch. Dermatol.*, vol. 120, No. 11, pp. 1466–1470 (1984).

Bach, et al., "Studies on the Possible Anti–Neoplastic Effect of Thalidomide", *ACTA Pathologic ET Microbiologica Scandinavica*, vol. 59, pp. 491–499 (1963).

Bach, et al., "Thalidomide in Cancer Chemotherapy", *The Lancet*, vol. 1, p. 1271 (1963).

Bahmer, F.A., "Therapie bei lymphozytischer Infiltration", *Der Hautarzt*, vol. 43, p. 663 (1992).

Balabanova, et al., "Lupus erythermatosus Hypertrophicus et Profundus", *Z. Hautkr.*, vol. 67, No. 9, pp. 812–815 (1992).

Barnes, et al., "Tumor Necrosis Factor Production in Patients with Leprosy", *Infection and Immunity*, vol. 60, No. 4, pp. 1441–1446 (1992).

(List continued on next page.)

*Primary Examiner*—Joseph K. McKane
*Assistant Examiner*—Sonya Wright
(74) *Attorney, Agent, or Firm*—Pennie & Edmonds LLP

(57) ABSTRACT

The invention provides new and useful analogs of 2-phthalimidinoglutaric acid. These analogs include DL-2-methyl-2-phthalimidinoglutaric acid and hydroxylated analogs of 2-phthalimidinoglutaric. The invention also provides processes for making these analogs. The invention also provides the two individual enantiomers of DL-2-methyl-2-phthalimidinoglutaric acid, (R)-(+)-2-methyl-2-phthalimidinoglutaric acid and (S)-(-)-2-methyl-2-phthalimidinoglutaric acid, and processes for separating these individual enantiomers from the racemate. Further, the invention provides methods for inhibiting angiogenesis and treating angiogenesis-associated diseases, including cancer and macular degeneration, by administering one or more of these compounds.

19 Claims, 14 Drawing Sheets

OTHER PUBLICATIONS

Barnhill, et al., "Thalidomide: Use and Possible Mode of Action in Reactional Lepromatous Leprosy and in Various Other Conditions", *J. Am. Acad. Dermatol.*, vol. 7, No. 3, pp. 317–323 (1982).

Barnhill, R. et al., "Studies on the Anti–inflammatory Properties of Thalidomide: Effects on Polymorphonuclear Leukocytres and Monocytes", *J. Am. Acad. Derm.*, vol. 11, No. 4, Part 1, pp. 814–819 (1984).

Barriere, H., "Traitement par la thalidomide", *La Presse Médicale*, vol. 12, No. 15, pp. 963 (1983).

Bazzoli, et al., "The Effects of Thalidomide and Two Analogues on the Regenerating Forelimb of the Newt", *J. Embryol. Exp. Morph.*, vol. 41, pp. 125–135 (1977).

Beck, Jr. et al. "Vascular Development: Cellular and Molecular Regulation", *The FASEB Journal*, vol. 11, pp. 365–374 (1997).

Beccerica, E., "L'approccio terapeutico al paziente anziano con artrite reumatoid", *Clin. Ter.*, vol. 122, pp. 289–298 (1987).

Belaube, P. et al., "Should Thalidomide be Rehabilitated?", *Sem. Hop. Paris*, vol. 59, No. 45, pp. 3101–3104 (1983).

Bensinger, W.I., "Supportive Care in Marrow Transplantation", *Curr. Opin. Oncol.*, vol. 4, No. 4, pp. 614–623 (1992).

Bernal, et al., "Cellular Immune Effects of Thalidomide in Actinic Prurigo", *Int'l. J. of Dermat.*, vol. 31, No. 8, pp. 599–600 (1992).

Blair, R. et al., "Human Mast Cells Stimulate Vascular Tube Formation", *Journal of Clinical Investigation*, vol. 99, No. 11, pp. 2691–2700 (1997).

Blaschke, V. et al., Chromatographische Racemattrennung von Thalidomid und tertogene Wirkung der Enantiomere, *Arzneimittel Forsch./Drug Res.*, vol. 29, No. II, pp. 1640–1642 (1979).

Bonifacino, J. et al., "A Peptide Sequence Confers Retention and Rapid Degradation in the Endoplasmic Reticulum", *Science*, vol. 2, pp. 79–80 (1990).

Bonnetblanc, et al., "Thalidomide and Recurrent Aphthous Stomatitis: a Follow–up Study", *Dermatology*, vol. 193, No. 4, pp. 321–323 (1996).

Boodman, S.G., "Question About a Popular Prenatal Test", *The Washington Post* (1992).

Bowers, et al., "Effect of Thalidomide on Orogenital Ulceration", *Br. Med. Journ.*, vol. 287, No. 6395, pp. 799–800 (1983).

Braun, et al., "Thalidomide Metabolite Inhibits Tumor Cell Attachment to Concanavalin a Coated Surfaces", *Biochem. Biophys. Res. Comm.*, vol. 98, No. 4, pp. 1029–1034 (1981).

Brem, H. et al., "Interstitial Chemotherapy with Drug Polymer Implants for the Treatment of Recurrent Gliomas", *J. Neurosurg.*, vol. 74, pp. 441–446 (1991).

Bressler, S. et al., "Clinicopathologic Correlation of Occult Choroidal Neovascularization in Age–Related Macular Degeneration", *Arch. Opthalmol.*, vol. 110, p. 827 (1992).

Brodthagen, H., "Significant Response of Oral Aphthosis to Thalidomide Treatment", *J. Am. Acad. Dermatol.*, vol. 13, No. 3, p. 509 (1985).

Brovarone, et al., "Occhio e gravidanza", *Minerva Ginecol.*, vol. 43, pp. 141–167 (1991).

Browne, M.J. et al., Expression of Recombinant Human Plasminogen and Aglycoplasminogen in HeLa Cells, *Fibrinolysis*, vol. 5, pp. 257–260 (1991).

Bubl, et al., "Dysphagia in Dermatologic Disease", *Dysphagia*, vol. 8, No. 2, pp. 85–90 (1993).

Buckley, C. et al., "Pyoderma Gangrenosum with Severe Pharyngeal Ulceration", *J. of Royal Society of Medicine*, vol. 83, pp. 590, 591 (1990).

Buelen, I., Treatment of a Grade II Astrocytoma with Thalidomide (Phthalylglutamic Acid Imide) [Behandlung eines Astrocytoms II. Grades mit Thaliodmid (N–Phthalylglutaminsäureimid)], *Arzneim.–Forsch.*, vol. 17, No. 5, pp. 646–648 (1967).

Bullock, W.E., "The Clinical Significance of Erythema Nodosum", *Hosp. Pract.*, vol. 21, No. 3, pp. 102E–2H, 102K–2L, 102Q–2R pas (1986).

Burger, et al., "Epidermolysis Bullosa Acquisita, a Rare Late Complication of Allogeneicbone Marrow Transplantation?", *Bone Marrow Transplant*, vol. 9, No. 2, pp. 139–141 (1992).

Burrows, N.P., "Thalidomide Modifies Disease", *Brit. Med. J.*, vol. 307, No. 6909, pp. 939–940 (1993).

Calnan, et al., "Actinic Prurigo (Hutchinson's Summer Prurigo)", *Clin. Exp. Dermatol.*, vol. 2, No. 4, pp. 365–372 (1977).

Cant, J.S., "Minor Ocular Abnormalities Associated With Thalidomide", *The Lancet*, p. 1134 (1966).

Carmichael, et al., "Thalidomide: A Restricted Role", *Lancet*, vol. 339, No. 8805, p. 1362 (1992).

Cashin, C.H. et al., "Angiogenesis and Chronic Inflammation", *Agents and Actions*, vol. 3/4, pp. 332–338 (1991).

Casini, G. et al., "Preparazione Di Uno Degli Antipodi Ottici Della 2–Ftalimmidoglutarimmide", *Il Pharmaco, Ed. Sc.*, vol. XIX, Fasc. 6, pp. 563–565 (1964).

Chapon, et al., "Neuropathies Caused by Thalidomide", *Rev. Neurol.*, vol. 141, No. 11, pp. 719–728 (1985).

Chen, T. et al., "Plasma Pharmacokinetics and Urinary Excretion of Thalidomide after Oral Dosing in Healthy Male Volunteers", *The Am. Society for Pharma. and Experi. Therapeutics*, vol. 17, No. 4, pp. 402–405 (1988).

Chosidow, O, et al., "Sclerodermatous Chronic Graft–Versus–Host Disease: Analysis of Sevencases", *J. Am. Acad. Dermatol.*, vol. 26, No. 1, pp. 49–55 (1992).

Claydon, et al., "Gastrointestinal Emergencies in HIV Infection", *Balliere's Clin Gastroennterol.*, vol. 5, No. 4, pp. 887–911 (1991).

Clemmensen, et al., "Thalidomide Neurotoxicity", *Arch. Dermatol*, vol. 120, No. 3, pp. 338–341 (1984).

Colville–Nash, P.R. et al., "Angiogenesis and rheumatoid arthritis: Pathogenic and Therapeutic Implications", *Ann. Rheum. Dis.*, vol. 51, pp. 919–925 (1992).

Congy, et al., "Plasma Zinc Levels in Elderly Patients Hospitalized in Long Stay Units. Correlations with Other Nutritional Markers, Immunological Tests and Survival", *Sem. Hop. Paris*, vol. 59, No. 45, pp. 3105–3108 (1983).

Costa, et al., "Aseptic Adenitis in a Patient with Pyoderma Gangrenosum", *Ann. Dermatol.*, vol. 121, No. 8, pp. 550–552 (1994) (Abstract Only).

Crain, E. et al., "The Effect of Thalidomide on Experimental Autoimmune Myasthenia Gravis", *J. of Autoimmunity*, vol. 2, pp. 197–202 (1989).

Crawford, C.L., "Letter: Thalidomide in Erythema Nodosum Leprosum", *Lancet*, vol. 2, No. 839, pp. 1201–1202 (1973).

Crawford, C.L., "Treatment of Erythema Nodosum Leprosum with Thalidomide", *Lancet*, vol. 2, No. 828, pp. 567–568 (1973).

Crawford, C.L., "Use of Thalidomide in Leprosy [letter; comment]", *BMJ*, vol. 302, No. 6729, pp. 1603–1604 (1991).

Crum, et al., "A New Class of Steroids Inhibits Angiogenesis in the Presence of Heparin or a Heparin Fragment", *Science*, vol. 230, pp. 1375–1378 (1985).

Current Bibliographics in Medicine, "Thalidomide: Potential Benefits and Risks", *National Inst. Health, National Library of Medicine*, pp. 1–72 (Jan. 1963–Jul. 1997).

Dark, et al., "Combretastin A–4, an Agent that Displays Potent and Selective Toxicity Toward Tumor Vasculature", *Cancer Research*, vol. 37, pp. 1829–1834 (1997).

David–Bajar, K.M., "Subacute Cutaneous Lupus Erythematosus", *J. Invest. Dermatol.* vol. 100, No. 1, pp. 2s–8s (1993).

D'Amato, R. J. et al., "Thalidomide is an Inhibitor of Angiogenesis", *Proc. Natl. Acad. Sci.*, vol. 91, pp. 4082–4085 (1994).

D'Amato, et al., "Angiogenesis Inhibition in Age–Related Macular Degeneration", *Opthalmology*, vol. 102, No. 9, pp. 1261–1262 (1995).

D'Amato, et al., "Microscopic Analysis of Retinal–Vessels Utilizing Fluorescein–Labeled High–Molecular–Weight Dextrans", *Invest. Opthamol. & Visual Science*, vol. 33, No. 4, p. 1082 (1992).

De, A.U. et al., "Possible Antineoplastic Agents I", *J. of Pharma. Sci.*, vol. 64, No. 2, pp. 262–266 (1975).

De Cock, K., "Treatment of Ulcerative Colitis", *Brit. Med. J.*, vol. 1, pp. 1356 (1979).

DeKlerk, et al., "New Methods of Treatment for Renal Allotransplants Using the Baboon as a Primate Experimental Model", *J. Urol.* vol. 102, No. 5, pp. 532–540 (1969).

Dhodapkar, et al., "A Phase II Pilot Study of Anti–Angiogenesis Therapy Using Thalidomide in Patients with Multiple Myeloma", *UARK 98–003*, PP. 1–15 Date not available.

Dicken, C. H., "Malignant pyoderma", *J. of the Am. Acad. of Dermatol.*, vol. 13, No. 6, pp. 1021–1025 (1985).

DiPaolo, et al., "Thalidomide: Effects on Ehrlich Ascites Tumor Cells in vitro", *Science*, vol. 144, pp. 1583 (1964).

DiPaolo, "Effect of Thalidomide on a Variety of Transplantable Tumors", *Cancer Chemo. Reports*, vol. 29, pp. 99–102 (1963).

DiPaolo, "In Vitro Test Systems for Cancer Chemotheraphy. II. Correlation of In Vitro Inhibition of Dehydrogenase and Growth with In Vivo Inhibition of Ehrlich Ascites Tumor", *P.S.E.B.M.*, vol. 114, pp. 384–387 (1963).

DiPaolo et al., "Teratogenesis–oncogenesis: A Study of Possible Relationships", *Arch. Path.*, vol. 81, pp. 3–56 (1966).

Dorveaux, et al., "Le Traitement Actuell du Lupus Erythemateux Chronique", *Le Concours Med.* vol. 106, No. 31, pp. 2957–2961 (1984).

Doutre, et al., "Pyoderma Gangrenosum and Hemopathies. A propos of 2 Cases", *Nouv Rev Fr Hematol*, vol. 29, No. 4, pp. 251–254 (1987).

Dunn, et al., "Bone Marrow Transplantation and Cataract Development", *Arch. Ophthalmol*, vol. 111, No. 10, pp. 1367–1373 (1993).

(Editorial) "Thalidomide in Dermatology and Leprosy", *Lancet*, vol. 2, No. 8446, pp. 80–81 (1985).

(Editorial) "Thalidomide Tested for Treatment of AIDS", *U.S. Pharm.*, vol. 18, No. 8, p. 14 (1993).

Eger, K. et al., "Synthesis, Central Nervous System Activity and Teratogenicity of a Homothalidomide", *Arzheim. Forsch/Drug Res.*, vol. 40 (II), No. 10, pp. 1073–1075 (1990).

Ehrlich, G.E., "Behcet's Disease: Current Concepts", *Comprehensive Therapy*, vol. 15, No. 1, pp. 27–30 (1989).

Elia, et al., "Giant Esophageal Ulcer Treated wtih Steroids in AIDS Patient(2)", *J. Acquired Immune Defic. Syndr.*, vol. 5, No. 8, pp. 848–849 (1992).

Eisenbud, L. et al., "Recurrent Aphthous Stomatitis of the Behcet's Type: Successful Treatment with Thalidomide", *Oral Surgery, Oral Medicine, Oral Pathology*, vol. 64, No. 3, pp. 289–292 (1987).

Eravelly, J. et al., "Thalidomide in Weber–Christian Disease", *The Lancet*, vol. 1, No. 8005, p. 251 (1977).

Eriksson, et al., "Drug Exposure and Flow Cytometry Anaylses in a Thalidomide Treatment Schedule that Prolongs Rat Cardiac Graft Survival", *Transplant Proc.*, vol. 24, No. 6, pp. 2560–2561 (1992).

Eriksson, S. O. et al., "Synthesis and Alkaline Hydrolysis of Some N–substituted Phthalimides", *Acta Pharm. Suecica*, vol. 10, pp. 63–74 (1973).

Fabro, S. et al., "The Metabolism of Thalidomide: Some Biological Effects of Thalidomide and its Metabolites", *Brit. J. PHarmacol.*, vol. 25, pp. 352–362 (1965).

Fabro, S. et al., "Teratogenic Activity of Thalidomide and Related Compounds", *Life Sci.*, vol. 3, pp. 987–992 (1964).

Fabro, S. M.D., "Biochemical Basis of Thalidomide Teratogenicity", *The Biochemical Basis of Chemical Teratogenesis*, Chapter 5, pp. 159–178 (1981).

Fajardo, et al., "Dual Role of Tumor Necrosis Facot–$\alpha$ in Angiogenesis", *Am. J. Pathol.*, vol. 140, No. 3, pp. 539–544 (1992).

Faure, et al., "PMN Leukocytes Chemotaxis: Inhibition by Thalidomide", *Pathol. Biol. (Paris)*, vol. 29, No. 10, pp. 601–604 (1981).

Faure, et al., "Inhibition of PMN Leukocytes Chemotaxis by Thalidomide", *Arch. Dermatol. Res.*, vol. 269, No. 3, pp. 275–280 (1980).

Fazal, N. et al., "Effect of Blocking TNF–$\alpha$ on Intracellular BCG (*Bacillus* Calmette Guerin) Growth in Human Monocyte–Derived Macrophages", *FEMS Microbiology Immunology*, vol. 105, pp. 337–346 (1992).

Fickentscher, K. et al., "Stereochemical Properties and Teratogenic Activity of Some Tetrahydrophthalimides", *Mol. Pharmacol.n*, vol. 13, pp. 133–141 (1997).

Field, E. O. et al., "Effect of Thalidomide on Splenomegaly (GVH Reaction: in the Chick Embryo. Treatment of Donor Cells Only", *Nature*, vol. 211, No. 5055, pp. 1309–1310 (1996).

Flohe, L. et al., "Studies on the Hypothetical Relationship of Thalidomide–induced Embryopathy and Collagen Biosynthesis", *Arzneimitte/Forschung (Germany West)*, vol. 31, No. 2, pp. 315–320 (1981).

Folkman, J. et al., "Angiogenesis", *J. Biol. Chem.*, vol. 267, No. 16, pp. 10931–10934 (1992).

Folkman, J. et al., "Angiogenesis Inhibition and Tumor Regression Caused by Heparin or a Heparin Fragment in the Presence of Cortisone", *Science*, vol. 221. pp. 719–725 (1983).

Folkman, J. et al., "Induction of Angiogenesis During the Transition from Hyperplasia to Neoplasis", *Nature*, vol. 339, pp. 58–61 (1989).

Folkman, J. et al., "Tumor Behavior in Isolated Perfused Organs: In Vitro Growth and Metastases of Biopsy material in Rabbit Thyroid and Canine Intestinal Segment", *Anals of Surgery*, pp. 491–502 (1966).

Folkman, J., "Tumor Angiogenesis: Therapeutic Implications", *The New England J. of Med.*, vol. 285, No. 21, pp. 1182–1186, (1971).

Folkman, J., "Angiogenesis and Its Inhibitors", *Important Advances in Oncology*, J.B. Lippincott H. Company, pp. 42–62 (1985).

Folkman, J., "Angiogenesis in Cancer, Vascular, Rheumatoid and Other Disease", *Nature Medicine*, vol. 1, No. 1, pp. 27–30 (1995).

Folkman, J., "What is the Evidence that Tumors are Angiogenesis Dependent?", *J. Naat' Cancer Inst.*, vol. 82, No. 1, (1990).

Francois, J., "Embryological Pigment Epithelial Dystrophies", *Opthalmologic*, vol. 172, pp. 417–433 (1976).

Fuller, et al., "Thalidomide, Peripheral Neruopathy and AIDS", *Int. J. STD AIDS*, vol. 2, No. 5, pp. 369–370 (1991).

Furner,, B.B., "Treatment of Subacute Cutaneous Lupus Erythematosus", *Int. J. Dermatol.*, vol. 29, No. 8, pp. 542–547 (1990).

Gad, et al., "Thalidomide Induces Imbalances in T–Lymphocyte Sub–Populations in the Circulating Blood of Healthy Males", *Lepr. Rev.*, vol. 56, No. 1, pp. 35–39 (1985).

Gaetani, M., "Studi Sull'Attivita Antitumorale Della Talidomide", *Giornale Italiano diu Chemioterapis*, pp. 83–86 Date not available.

Gehanno, et al., "Mouth and Pharyngeal Hyperalgesic Syndromes in AIDS", *Ann. Otolarygol Chir. Cervicofac*, vol. 107, No. 5, pp. 311–313 (1990).

Genvo, et al., "Treatment of Aphthosis with Thalidomide and with Colchicine", *Dermatologica*, vol. 168, No. 4, pp. 182–188 (1984).

Geoghiou, et al., "HIV–Associated Oesophageal Ulcers Treated with Thalidomide", *Med. J. of Australia*, vol. 152, pp. 382–383 (1990).

Gershbein, "Effect of Transplated Tumor and Various Agents on Liver Regeneration During Pregnancy", *P.S.E.B.M.*, vol. 126, pp. 88–92 (1967).

Gershbein, L. L., "The Thalidomide Analog, EM 12, Enhances 1,2–dimethylhydrazine–induction of Rat Colon Adenocarcinomas", *Canc. Ltrs*, vol. 60, pp. 129–133 (1991).

Gershbein, L. L., "Effect of Various Agents on Liver Regeneration and Walker Tumor Growth in Partially Hepatectomized Rats", *Canc. Res.*, vol. 26, No. 9, pp. 1905–1908 (1966).

Ghigliotti, G. et al., "Thalidomide: Treatment of Choice for Aphthous Ulcers in Patients Seropositive for Human Immunodeficiency Virus", *J. of the Am. Acad. of Dermatol.*, vol. 28, No. 2, Part I, pp. 271–272 (1993).

Gimbrone, M.A. et al., "Tumor Dormancy in Vivo by Prevention of Neovasularization", *Journal of Experimental Medicine*, vol. 136, pp. 261–276 (1972).

Gimbrone, M. A. et al., "Tumor Growth and Neovascularization: An Experimental Model Using the Rabbit Cornea", *J. Nat. Canc. Instit.*, vol. 52, No. 2, pp. 413–419 (1974).

Goihman–Yahr, Mauricio et al., "Significance of Neutrophil Activation in Reactional Lepromatous Leprosy: Effects of Thalidomide in vivo and in vitro. Activation in Adjuvant Disease", *Int. Archs. Allergy Appl. Immun.*, vol. 57, pp. 317–332 (1978).

Goihman–Yahr, M., et al., "Autoimmune Diseases and Thalidomide II. Adjuvant Disease, Experimental Allergic Encephalomyelitis and Experimental Allergic Neuritis of the Rat", *Int. J. Leprosy*, vol. 42, No. 3, pp. 266–275 (1974).

Gorin, I.,et al., "Thalidomide May Cure AIDS Ulcers", *Nurs. Times*, vol. 86, No. 24, p. 10 (1990).

Gorin, I., et al., "Thalidomide in Hyperalgic Pharyngeal Ulceration of AIDS", *Lancet*, vol. 335, p. 1343 (1990).

Goulden, V., et al., "Linear Prurigo Simulating Dermatitis Artefacta in Dominant Dystrophicepidermolysis Bullosa", *Br. J. Dermatol.*, vol. 129, No. 4, pp. 443–446 (1993).

Grabstad, H. et al., "Clinical Experiences with Thalidomide in Patients with Cancer", *Clinical Pharmacol. and Therapeutics*, vol. 6, pp. 298–302 (1965).

Grant, D.S. et al., "Scatter Factor Induces Blood Vessel Formation in vivo", *Proc. Natl. Acad. Sci.*, vol. 90, pp. 1937–1941 (1993).

Grinspan, et al., "Treatment of Aphthae with Thalidomide", *J. Am. Acad. Dermatol.*, vol. 20, No. 6, pp. 1060–1063 (1989).

Grinspan, D., "Significant Response of Oral Aphthosis to Thalidomide Treatment", *Am. Acad. of Dermatol.*, vol. 12, No. 1, Part 1, pp. 85–90 (1985).

Grosshans, E., et al., "Thalidomide Therapy for Inflammatory Dermatoses", *Int. J. Dermatol*, vol. 23, No. 9, pp. 598–602 (1984).

Guidetti, E., et al., "Ricerche Sull' azione Immunodepressiva Della Talidomide e del Prednisolone in Ratti Portatori Di Neoplasie Sperimentalmente Indotte", *Cancro*, vol. 22, pp. 503–512 (1969).

Günzler, V., "Thalidomide in Human Immunodeficiency Virus (HIV) Patients. A Review of Safety Considerations", *Drug Saf*, vol. 7, No. 2, pp. 116–134 (1992).

Günzler, V., "Thalidomide–A Therapy for the Immunological Consequences of HIV Infection?", *Medical Hypotheses*, vol. 30, No. 2, pp. 105–109 (1989).

Gutiérrez–Rodriguez, O. et al., "Treatment of Refractory Rheumatoid Arthritis–The Thalidomide Experience", *The J. of Rheumatology*, vol. 16, No. 2, pp. 158–163 (1989).

Gutiérrez–Rodriguez, O. et al., "Thalidomide A Promising New Treatment for Rheumatoid Arthritis", *Arthritis and Rheumatism*, vol. 27, No. 10, pp. 1118–1121 (1984).

Haffner, M.E. M.D., "Studies Involving Orphan Products for Treating/Diagnosing Women's Diseases", *Food and Drug Law Journal*, vol. 48, pp. 205–211 (1992).

Hamza, M. M.D., "Behcet's Disease, Palmoplantar Pustulosis and HLA–B27 Treatment with Thalidomide", *Clinical and Experimental Rheumatology*, vol. 8, No. 4, p. 427 (1990).

Hamza, M.H., "Treatment of Behcet's Disease with Thalidomide", *Clinical Rheumatol.*, vol. 5, No. 3, pp. 365–371 (1986).

Handley, J. et al., "Chronic Bullous Disease of Childhood and Ulcerative Colitis", *Pediatric Dermatol.*, vol. 10, No. 3, pp. 256–258, (1993).

Harindra, et al., "Papulo–Pruritic Eruption and Giant Ulceration of the Mouth: A Difficult Clinical Feature to Treat in the Patient Infected with Humanimmunodeficiency Virus(1)", *Arch. Intern. Med.*, vol. 152, No. 9, p. 1924 (1992).

Harris, A., "Antiangiogenesis for Cancer Therapy", *Lancet*, vol. 349 (Suppl. II), pp. 13–15 (1997).

Hasper, M.F., "Chronic Cutaneous Lupus Erythematosus. Thalidomide Treatment of 11 Patients", *Arch. Dermatol*, vol. 19, No. 10, pp. 812–815 (1983).

Hasper, M.F., et al., "Thalidomide in the Treatment of Chronic Discoid Lupus", *Acta. Derm. Venereol*, vol. 62, No. 4, pp. 321–324 (1982).

Hastings, R.C., et al., "Thalidomide in the Treatment of Erythema Nodosum Leprosum. With a Note on Selected Laboratory Abnormalities in Erythema Nodosum Leprosum", Clin. Pharmacol. Ther., vol. 11, No. 4, pp. 481–487 (1970).

Hatfill, S.J. et al., "Induction of Morphological Differentiation in the Human Leukemic Cell Line K562 by Exposure to Thalidomide Metabolites", Leukemia Res., vol. 15, No. 2/3, pp. 129–136 (1991).

Hayashi, S. et al., "A Synthetic Peptide for α Chemokines Inhibits the Growth of Melanoma Cell Lines", J. Clin. Invest., vol. 99, No. 11, pp. 2581–2587 (1997).

Heaton, et al., "Graft–versus–Host Disease Following Liver Transplantation", J. R. Soc. Med., vol. 85, No. 6, pp. 313–314 (1992).

Hellman, K. et al., Prolongation of Skin Homograft Survival by Thalidomide, Brit. Med. J., vol. 2, pp. 687–689 (1965).

Helm, F. –Ch. et al., "Comparative Teratological Investigation of Compounds Structurally and Pharmacologically Related to Thalidomide", Arzneim.–Forsch./Drug Res., vol. 31 (I), No. 6, pp. 941–949 (1981).

Hendler, S. S. et al., "Thalidomide for Autoimmune Disease", Medical Hypotheses, vol. 10, pp. 437–443 (1983).

Heney, D. et al., "Thalidomide Treatment for Chronic Graft–Versus–Host Disease", Biomed. Pharmacother, vol. 44, No. 4, pp. 199–204 (1990).

Heney, D., et al., "Thalidomide for Chronic Graft–versus–Host Disease in Children", Lancet, vol. 2, No. 8623, p. 1317 (1988).

Hojyo, et al., "Actinic prurigo (9)", Int. J. Dermatol., vol. 31, No. 5, pp. 372–373 (1992).

Holm, et al., "Chronic Cutaneous Lupus Erythematosus Treated with Thalidomide", Arch. Dermatol., vol. 129, No. 12, pp. 1548–1550 (1993).

Hori, A. et al., "Suppression of Solid Tumor Growth by Immunoneutralizing Monoclonal Antibody against Human Basic Fibroblast Growth Factor", Canc. Res., vol. 51, pp. 6180–6184 (1991).

Hu, D.E., "Inhibition of Angiogenesis in Rats by IL–1 Receptor Antagonist and Selected Cytokine Antibodies", Inflammation, vol. 18, pp. 45–58 (1994).

Hu, J. et al., "A Novel Regulatory Function of Proteolytically Cleaved VEGF–2 for Vascular Endothelial and Smooth Muscle Cells", The FASEB Journal, vol. 11, pp. 498–504 (1997).

Ingber, D. et al., "Synthetic Analogues of Fumagillin that Inhibit Angiogenesis and Suppress Tumor Growth", Ltrs. to Nat., vol. 348, pp. 555–557 (1990).

Ingber, D., "Drug News and Trial Developments", AIDS Patient Care, vol. 6, No. 6, p. 288 (1992) Randall, T., "Thalidomide's Back in the News, but in more Favorable Circumstances", JAMA, vol. 263, No. 11, pp. 1467–1468 (1990).

Jacobson, J. et al., "Thalidomide for the Treatment of Oral Aphthous Ulcers in Patients with Human Immunodeficiency Virus Infection", The New England Journal of Medicine, vol. 336, No. 21, pp. 1487–1493 (1997).

Jacobson, et al., "The Diagnosis and Treatment of Leprosy", South Med.. J., vol. 69, No. 8, pp. 979–985 (1976).

Jager, et al., "Clinical Observations in the Treatment of Leprosy Reaction with Cyclic Imides", Int. J. Lepr. Other Mycobact Dis., vol. 39, No. 2, p. 589 (1971).

Jeltsch, M. et al., "Hypeplasia of Lymphatic Vessels in VEGF–C Transgenic Mice", Science, vol. 276, pp. 1423–1426 (1997).

Jenkins, et al., "Thalidomide, Orogenital Ulcers, and Risk of Teratogenicity", The Lancet, vol. 1, No. 8417–18, p. 511 (1985).

Jenkins, et al., "Thalidomide in Severe Orogenital Ulceration", The Lancet, vol. 2, No. 8417–18, pp. 1424–1426 (1984).

Jennings, et al., "Effects of Actinomycin D on the Production of Acute Phase Protein in the Rabbit", Experienta, vol. 25, pp. 305–306 (1969).

Jew, et al., "Thalidomide in Erythema Nodosum Leprosum", DICP, vol. 24, No. 5, pp. 482–483 (1990).

Johnke, et al., "Thalidomide Treatment of Prurigo Nodularis", Ugeskr Laeger, vol. 155, No. 38, pp. 3028–3030 (1993) (Abstract Only).

Jönsson, N., "Chemical Structure and Teratogenic Propeties IV. An Outline of a Chemical Hypothesis for the Teratogenic Action of Thalidomide", Acia Pharm. Succica, vol. 9, pp. 543–562 (1972).

Jönsson, N., "Chemical Structure and Teratogenic Properties I. Synthesis and Teratogenic Activity in Rabbits of some Derivatives of Phthalidmide, Isoindoine–1–one, 1.2–Benzisothiazoline–3–one–1, 1–Dioxide and 4(3II)–Quinazolinone", Acia Pharm Succica, vol. 9, pp. 431–436 (1972).

Jönsson, N., "Chemical Structure and Teratogenic Properties III a Review of Available Data on Structure–Activity Relationships and Mechanism of Action of Thalidomide Analogues", Acia Pharm. Succia, vol. 9, pp. 521–542 (1972).

Jorizzo, et al., "Thalidomide Effects in Behcet's Syndrome and Pustular Vasculitis", Arch. Intern. Med., vol. 146, No. 5, pp. 878–881 (1986).

Juret, et al., "Absence d'effet Carcino–Frénateur du Talidomide vis–á–vis de deux Tumerus Greffées", Société de Biologie, vol. 23, pp. 246–249 (1963).

Kaitin, K.I., "Graft–versus–Host Disease", N. Engl. J. Med., vol. 325, No. 5, pp. 357–358 (1991).

Kaplan, G. et al., "TNFα regulation of HIV1: Biology and Therapy", Res. in Immunology, vol. 145, No. 8–9, pp. 685–690 (1994).

Katsuta, et al., "Carcinogenesis in Tissue Culture. 3. Effects of the Second Treatments on DAB–Induced Proliferating Liver Cells of Normal Rats in Culture", Jpn. J. Exp. Med., vol. 35, No. 4, pp. 231–248 (1965).

Keenan, R.J. et al., "Immunosuppressive Properties of Thalidomide", Transplantation, vol. 52, No. 5, pp. 908–910 (1991).

Kenyon, et al., "The Discovery of New Inhibitors of Angiogenesis Using an Improved Mouse Corneal Neovascularization Model", No. 459–367, p. S94 (Abstract only) Date not available.

Kim, K. J. et al., "Inhibition of Vascular Endothelial Growth Factor–Induced Angiogenesis Suppresses Tumor Growth in vivo", Ltrs. to Nat., vol. 362, pp. 841–844 (1993).

Kitamoto, Y. et al., "Vascular Endothelial Growth Factor is an Essential Molecule for Mouse Kidney Development: Glomerulogenesis and Nephrogenesis", J. Clin.. Invest., vol. 99, No. 10, pp. 2351–2357 (1997).

Knighton, D. et al., "A vascular and Vascular Phases of Tumor Growth in the Chick Embryo", Br. J. Can., vol. 35, pp. 347–356 (1977).

Knop, et al., "Thalidomide in the Treatment of Sixty Cases of Chronic Discoid Lupus Erythematosus", *Br. J. Dermatol*, vol. 108, No. 4, pp. 461–466 (1983).

Koch, H.P. et al., "4 Thalidomide and Congeners as Anti–inflammatory Agents", *Progress in Medicinal Chemistry*, vol. 22, pp. 166–242 (1985).

Korn, et al., "The Second International Workshop on Scleroderma Research", *Matrix*, vol. 13, No. 5, pp. 427–429 (1993).

Kroger, et al., "Synergistic Effects of Thalidomide and Poly (ADP–ribose) Polymerase Inhibition on Type II Collagen–Induced Arthritis in Mice", *Inflammation*, vol. 20, pp. 203–215 (1996).

Kundu, et al., "Prurigo Nodularis in an HIV Positive Man (2)", *Genitourinary Medicine*, vol. 71, No. 2, pp. 129–130 (1995).

Kürkcüoglu, N. et al., "Thalidomide in the treatment of Recurrent Necrotic Mucocutaneous Aphthae", *Brit. J. of Dermatol.*, vol. 112, No. 5, pp. 632 (1985).

Lane, et al., "Treatment of Actinic Prurigo with Intermittent Short–Course Topical 0.05% Clobetaso 17–Propionate. A Preliminary Report", *Arch. Dermatol*, vol. 126, No. 9, pp. 1211–1213 (1990).

Languillon, J., "The Effects of Thalidomide on Leprosy Reaction", *Int. J. Lepr. Other Mycobact. Dis.*, vol. 39, No. 2, pp. 590–592 (1971).

Larsson, H., "Treatment of Severe Colitis in Behcet's Syndrome with Thalidomide (CG–217)", *J. of Intern. Med.*, vol. 228, pp. 405–407 (1990).

Ledo, E., "Photodermatosis. Part I: Photobiology, Phtoimmunology, and Idiopathicphotodermatoses", *Int. J. Dermatol.*, vol. 32, No. 6, pp. 387–396 (1993).

Lehner, T., et al., "Thalidomide, Orogenital Ulcers, and the Risk of Teratogenesis", *The Lancet*, vol. 8423, pp. 288–289 (1985).

Lenicque, "Action of Thalidomide on the Induction of Tentacles in Regenerating Hydra Littoralis", *Acta. Zool.*, pp. 127–139 (1967).

Levy, et al., "Treatment of Erythema Nodosum Leprosum with Thalidomide", *The Lancet*, vol. 2, No. 824, pp. 324–325 (1973).

Lien, W. M. et al., "The Blood Supply of Experimental Liver Metastases. II. A microcirculatory Study of the Normal and Tumor Vessels of the Liver with the Use of Perfused Silicone Rubber", *Surgery*, vol. 68, No. 2, pp. 334–340 (1970).

Lo et al., "Treatment of Discoid Lupus Erythematosus", *Int. J. Dermatol.*, vol. 28, No. 8, pp. 497–507 (1989).

London, F., "Thalidomide in the Treatment of Actinic Prurigo", *Int. J. Dermatol.*, vol. 12, No. 5, pp. 326–328 (1973).

Lopez, J. et al., "Thalidomide as Therapy for Intestinal Chronic GVHD", *Bone Marrow Transplantation*, vol. 11, No. 3, pp. 251–252 (1993).

Louzir, B. et al., "Erythroleucemie chez un patient ayant une maladie de Behcet et traite au long cours par thalidomine", *Annales de Medecine Interne*, vol. 143, pp. 479–480 (1992).

Lueprasitsakul, W. et al., "Effect of Thalidomide on the Incidence of Iodine–Induced and Spontaneous Lymphocytic Thyroiditis and Spontaneous Diabetes Mellitus in the BB/Wor Rat", *Acta Endocrino Logica*, vol. 123, pp. 79–83 (1990).

Lüers, H., "Failure of Mutagenic Action of Thalidomide in Drosophila", *The Lancet*, vol. II, No. 7258, p. 1332 (1962).

Mangana–Garcia, M., "Antimalarials for Children", *J. Am. Acad. Dermatol*, vol. 30, No. 3, p. 510 (1994).

Maione, T. E. et al., "Inhibition of Angiogenesis by Recombinant Human Platelet Factor–4 and Related Peptides", *Science*, vol. 2, pp. 77–78 (1990).

Makonkawkeyoon, S. et al., "Thalidomide Inhibits the Replication of Human Immunodeficiency virus type 1", *Proc. Natl. Acad. Sci.*, vol. 90, pp. 5974–5978 (1993).

Marin–Padilla, M. et al. "Thalidomide Induced alterations in the Blastocyst and Placenta of the Armadillo, Dasypus Novemcinctus Mexicanus, Including a Choriocarcinoma", *The Am. J. of Pathol.*, vol. 43, No. 6, pp. 999–1016 (1963).

Mascaro, et al., "Thalidomide in the Treatment of Recurrent, Necrotic, and Giant Mucocutaneous Aphthae and Aphthosis", *Arch. Dermt.*, vol. 115, pp. 636–637 (1979).

Matsubara, et al., "Inhibition of Human Endothelial Cell Proliferation by Gold Compounds", *J. Clin. Invest.*, vol. 79, pp. 1440–1446 (1987).

Mauád, "Melhoras Clínicas Obtidas em Doentes Cancerosos Avançados com Tratamento Pela Talidomida Associada a Hormônios", *Anais Paulistas Medicina e Cirurgia*, pp. 15–39 (1963).

Maurice, et al., "The Effect of Thalidomide on Arachidonic Acid Metabolism in Human Polymorphonuclear Leukocytes and Platelets", *Br. J. Dermatol.*, vol. 115, No. 6, pp. 677–680 (1986).

McCarthy, et al., "Thalidomide for the Therapy of Graft–versus–Host Disease Following Allogeneic Bone Marrow Transplantation", *Biomed. Pharmacother*, vol. 43, No. 9, pp. 693–697 (1989).

McKenna, et al., "Linear IgA Disease, Oral Ulceration and Crohn's Disease", *Br. J. Dermatol*, vol. 127, pp. 67–68 (1992).

Meza, D. et al., "Managing the Gastronintestinal Complications of AIDS", *Drug Therapy*, vol. 23, No. 11, pp.m 74–83 (1993).

Miller, et al., "Zusammentreffen Einer Thalidomid–Induzierten Fehlbildung mit Einem Malignen Lymphom Hohen Malignitätsgrades", *Monatsschr. Kinderheilkd.*, vol. 128, pp. 27–29 (1980).

Miller, et al., "Treatment of Chronic Erythema Nodosum Leprosum with Cyclosporine A Produces Clinical and Immunohistologic Remission", *Int. J. Lepr. Other Mycobact. Dis.*, vol. 55, No. 3, pp. 441–449 (1987(.

Misery, L. et al., "Remission of Langerhans Cell Histiocytosis with Thalidomide Treatment", *Clinical and Experimental Dermatol.*, vol. 18, No. 5, p. 487 (1993).

Miura, M. et al., "Potentiating Effect of Thalidomide on Methylcholanthrene Oncogenesis in Mice", *Experimental Dermatol.*, vol. 18, No. 5, p. 487 (1970).

Miyachi, Y., "A Possible Mechanism of Action of Thalidomide on Rheumatoid Arthritis", *Arthritis and Rheuma.*, vol. 28, No. 7, p. 836 (1985).

Miyachi, et al., "Effects of Thalidomide on the Generation of Oxygen Intermediates by Zymosan–Stimulated Normal Polymorphonuclear Leukocytes", *Arch. Dermatol. Res.*, vol. 274, Nos. 3–4, pp. 363–367 (1982).

Mohri, et al., "Negative Effect of Thalidomide and Relative Substances on the Growth of HeLa Cells", *Chem. Pharm. Bull.*, vol. 16, pp. 2289–2292 (1968).

Moncada, et al., "Thalidomide–Effect on T Cell Subsets as a Possible Mechanism of Action", *Int. J. Lepr. Other Mycobact. Dist.*, vol. 53, No. 2, pp. 201–205 (1985).

Montrucchio, et al., "Tumor Necrosis Factor α–Induced Angiogenesis Depends on In Situ Platelet–Activating Factor Biosynthesis", *J. Exp. Med.*, vol. 180, pp. 377–382 (1994).

Moulin, et al., "Treatment of Jessner–Kanof Disease with Thalidomide", *Ann. Dermatol Venereol*, vol. 10, No. 8, pp. 611–614 (1983).

Mshana, et al., "Thymus–Dependent Lymphocytes in Leprosy. II. Effect of Chemotherapy on T–Lymphocyte Subpopulations", *J. Clin. Immunol.*, vol. 2, No. 2, pp. 69–74 (1982).

Mückter, et al., "Thalidomide and Tumor", *Antimicrobial Agents and Chemotherapy*, pp. 531–538 (1965).

Mummery, C.L. et al., "Screening for Cytoxicity in Neuroblastoma Cells–I. Dependence of Growth Inhibition on the Presence of Serum", *Toxicology Letters*, vol. 18, pp. 201–209 (1983).

Munro, et al., "Pyoderma Gangrenosum Associated with Behcet's Syndrome–Response to Thalidomide", *Clin. Exp. Dermatol.*, vol. 13, No. 6, pp. 408–410 (1988).

Muthukkaruppan, Vr. et al., "Angiogenesis in the Mouse Cornea", *Science*, vol. 205, No. 28, pp. 1416–1418 (1979).

Naafs, B. et al., "Thalidomide Therapy An Open Trial", *Intl. J. of Dermatol.*, vol. 24, No. 2, pp. 131–134 (1985).

Naafs, B., Bangkok Workshop on Leprosy Research. Treatment of Reactions and Nerve Damage. *Int. J. Lepr. Other Mycobact. Dis.*, vol. 64, No. 4, Suppl. S21–28 (1996).

Neubert, "Teratogenicity: Any Relationship to Carcinogenicity?", *Institute for Toxicology and Embryopharmacolgy, Free University of Berlin, Berlin, Federal Rep. Of Germany*, pp. 169–178 Date not available.

Nguyen, M. et al., "Elevated Levels of the Angiogenic Peptide Basic Fibroblast Growth Factor in Urine of Bladder Cancer Patients", *J. of the Natl. Canc. Inst.*, vol. 85, No. 3, pp. 241–242 (1993).

Nicholas, J., et al., "Interferon Alfa Therapy in Severe Unresponsive Subacute Cutaneous Lupus Erythematosus", *New Engl. J. Med.*, vol. 321, No. 22, pp. 1550–1551 (1989).

Nicolau, et al., "Thalidomide: Treatment of Severe Recurrent Aphthous Stomatitis in Patients with AIDS", *DICP*, vol. 24, No. 11, pp. 1054–1056 (1990).

Nielsen, et al., "Thalidomide Enhances Superoxide Anion Release from Human Polymorphonuclear and Leukocytes", *Acta. Pathol. Microbiol. Immunol. Scand.* [C], vol. 94, No. 6, pp. 233–237 (1986).

Obeso, J. et al., "Methods in Laboratory Investigation A Hemangioendothelioma–Derived Cell Line: Its Use as a Model for the Study of Endothelial Cell Biology", *Laboratory Investigation*, vol. 63, No. 2, pp. 259–269 (1990).

Oikawa, T. et al., "Eponenycin, A Novel Antibiotic is a Highly Powerful Angiogenesis Inhibitor", *Biochem. and Biophy. Res. Comm.*, vol. 181, No. 3, pp. 1070–1077 (1991).

Olson, et al., "Thalidomide (N–phthaloylglutamimide) in the Treatment of Advanced Cancer", *Clin. Pharmacol. Therap.*, vol. 6, No. 3, pp. 292–297 (1965).

Orzalesi, M., "Il Danno Iatrogeno in Neonatologica", *Ped. Med. Chir.*, vol. 14, pp. 105–112 (1992).

Ostraat, et al., "Thalidomide Prolongs Graft Survival in Rat Cardiac Transplants", *Transplant Proc.*, vol. 24, No. 6, pp. 2624–2625 (1992).

Otsuka, et al., "A New Potent Angiogenesis Inhibitor, FR–118487", *J. of Microbiol. and Biotechno.*, vol. 1, No. 3, pp. 163–168 (1991).

Paller, et al., "Proceedings of the Concurrent Sessions", *Pediatr. Dermatol*, vol 9, No. 4, pp. 397–406 (1992).

Passaniti, A. et al., "Methods in Laboratory Investigation A Simple, Quantitative Method for Assessing Angiogenesis and Antiangiogenic Agents Using Reconstitued Basement Membrane, Heparin, and Fibroblast Growth Factor", *Laboratory Investigation*, vol. 67, No. 4, pp. 519–528 (1992).

Patey, O. et al., "Thalidomide et colite ulcereuse dans la maladie de Behcet", *Gastroenterol. Clin. Biol.*, vol. 13, pp. 104–110 (1989).

Pearson, et al., "Treatment of Moderately Severe Erythema Nodosum Leprosum with Thalidomide—A Double–Blind Controlled Trial", *Lepr. Rev.*, vol. 40, No. 2, pp. 111–116 (1969).

Peyron, et al., "The Pharmacological Basis for the Treatment of Photodermatoses", *Biochimie*, vol. 68, No. 6, pp. 899–904, (1986).

Pfordte, "Über die Beeinflussung des Seruproperdinsystems Durch Verschiedene Arzneimittel", *Pharmazie*, vol. 26, pp. 301–302 (1971).

Phillips, et al., "Tumor Necrosis Factor Alpha (rhTNF) Fails to Stimulate Angiogenesis in the Rabbit Cornea", *Anatomical Rec.*, vol. 245, pp. 53–56 (1996).

Powell, R.J. et al., "Investigation and Treatment of Orogenital Ulceration; studies on a Possible Mode of Action of Thalidomide", *Brit. J. of Dermatol.*, vol. 113, Supp. 28, pp. 141–144 (1985).

Prigent, F. et al., "Sarcoidose cutanee Traitement par la Thalidomide", *La Presse Medicale*, vol. 12, No. 47, p. 3007 (1983).

Proenca, N.G., "Thalidomide: An Eclectic Medication in Dermatology", *Rev. Paul. Med.*, vol. 107, No. 1, pp. 41–46, (Abstract Only) (1989).

Radeff, et al., "Recurrent Aphthous Ulcer in Patient Infected with Human Immunodeficiency Virus: Successful Treatment with Thalidomide", *J. Am. Acad. Dermatol*, vol. 23, No. 3, pt. 1, pp. 523–525 (1990).

Rainsford, K.D., "Disease–Modifying Antirheumatic and Immunoregulatory Agents", *Bailliere's Clinical Rheumatology*, vol. 4, No. 3, pp. 405–432 (1990).

Rajan, et al., "A Clinical Study of Thalidomide Comparing Pre–Treatment and Post–Treatment Reactional Episodes and Corticosteroid Requirements", *Lepr. India*, vol. 55, No. 1, 111–116 (1983).

Randall, T., "Investigational New Drug (US) 'Orphan' Trials now Use Thalidomide from two Sources", *JAMA*, vol. 263, No. 11, p. 1474 (1990).

Revuz, J., "Actualite Du Thalidomide", *Ann. Dermatol. Venereol.*, vol. 117, pp. 313–321 (1990).

Revuz, J. et al, "Crossover Study of Thalidomide vs. Placebo in Severe Recurrent Aphthous Stomatitis", *Arch. Dermatol*, vol. 126, pp. 923–927 (1990).

Rhoton, A.J., "Role for Thalidomide in Primary Biliary Cirrhosis Treatment?", *Gastroenterology*, vol. 105, No. 3, p. 956 (1993).

Robbins, K. C., "The Plasminogen–Plasmin Enzyme System", *Fibrinolysis*, pp. 340–357 (??) Date not available.

Roe, F.J.C., "Pathology Thalidomide and Neoplasia", *Nature*, vo. 200, pp. 1016–1017 (1963).

Roe, et al., "Tumour–Incidence in Progeny of Thalidomide–Treated Mice", *British J. Cancer*, pp. 331–333, (1965).

Ruggenini, et al., "Thalidomide e Tumori Sperimentali", *Cancro*, vol. 20, pp. 39–55 (1967).

Rustin, et al., "Pyoderma Gangrenosum Associated with Behcet's Disease: Treatment with Thalidomide", *J. Am. Acad. Dermatol*, vol. 23, No. 5, Pt. 1, pp. 941–944 (1990).

Ryan, et al., "Thalidomide to Treat Esophageal Ulcer in AIDS (6)", *New Engl. J. Med.*, vol. 327, No. 3. pp. 208–209 (1992).

Salven, P. et al., "Serum Vascular Endothelial Growth Factor Is Often Elevated in Disseminated Cancer", *Clinical Cancer Research*, vol. 3, pp. 647–651 (1997).

Sampaio, et al., "Prolonged Treatment with Recombinant Interferon Gamma Induces Erythema Nodusum Lepromatous Leprosy Patients", *J. Exp. Med.*, vol. 175, No. 6, pp. 1729–1737 (1992).

Sampaio, et al., "Thalidomide Selectively Inhibits Tumor Necrosis Factor Alpha Production by Stimulated Human Monocytes", *J. Exp. Med.*, vol. 173, No. 3, pp. 699–703 (1991).

Santis, H.R., "Aphthous Stomatitis and its Management", *Curr. Opin. Dent*, vol. 1, No. 6, pp. 763–768 (1991) (Abstract Only).

Santos, et al., "In Vitro Tumor Necrosis Factor Production by Mononuclear Cells from Lepromatous Leprosy Patients and from Patients with Erythema Nodosumleprosum", *Clin. Immunol. Immunopathol.*, vol. 67, No. 3 I, pp. 199–203 (1993).

Sato, K. et al., "Increased Concentration of Vascular Endothelial Growth Factor/Vascular Permeability Factor in Cyst Fluid of Enlarging and Recurrent Thyroid Nodules", *Journal of Clinical Endocrinology and Metabolism*, vol. 82, No. 6, pp. 1968–1972 (1997).

Schweigerer, L. et al., "Angiogenesis and Angiogenesis Inhibitors in Paediatric Diseases", *European J. of Pediatric*, vol. 151, pp. 472–476 (1992).

Shannon, et al., "Inhibition of de Novo IgM Antibody Synthesis by Thalidomide as a Relevant Mechanism of Action in Leprosy", *Scand. J. Immunol.*, vol. 13, No. 6, pp. 553–562 (1981).

Shannon, et al., "Thalidomide's Effectiveness in Erythema Nodosum Leprosum is Associated with a Decrease in CD4+ Cells in the Peripheral Blood", *Lepr. Rev.*, vol. 63, No. 1, pp. 5–11 (1992).

Shealy, Y.F. et al., "D–and L–Thalidomide", *Chemistry and Industry*, pp. 1030–1031 (1965).

Sheehan, N.J., "Thalidomide Neurotoxicity and Rheumatoid Arthritis", *Arthritis and Rheuma.*, vol. 29, No. 10, p. 1296 (1986).

Sherman, M. et al., "Thalidomide: A Twenty–Five Year Perspective", *Food Drug Cosmetic Law J.*, vol. 41, pp. 458–466 (1986).

Sheskin, J., "The Treatment of Lepra Reaction in Lepromatous Leprosy. Fifteen Year's Experience with Thalidomide", *Int. J. Dermatol.*, vol. 19, No. 6, pp. 318–322 (1980).

Sheskin, et al., "In Vivo Measurements of Iron, Copper and Zinc in the Skin of Prurigo Nodularis Patients Treated with Thalidomide", *Dermatologica*, vol. 162, No. 2, pp. 86–90 (1981).

Shi, G. et al., "Kringle Domains and Plasmin Denaturation", *Biochem. and Biophy. Res. Comm.*, vol. 178, No. 1, pp. 360–368 (1991).

Sidky, Y. et al., "Inhibition of Angiogenesis by Interferons: Effects on Tumor–and Lymphocyte–induced Vascular Responses", *Canc. Res.*, vol. 47, pp. 5155–5161 (1987).

Silverman, W.A., "Medical Inflation", *Persp. Biol. Med.*, pp. 617–637 (1980).

Smith, et al., "Studies on the Relationship Between the Chemical Structure and Embryotoxic Activity of Thalidomide and Related Compounds", *Chemical Structure and Embryopathy*, pp. 194–209 Date not available.

Srivastava A. et al., "The Prognostic Significance of Tumor Vascularity in Intermediate–Thickness Skin Melanoma", *Am. J. Pathol.*, vol. 133, pp. 419–423 (1988) (abstract from MEDLINE: Accession No. 06745734).

Style, A., "Early Diagnosis and Treatment of Leprosy in the United States", *American Family Physician*, vol. 52, No. 1, 172–178 (1995).

Sugiura, et al., "Effect of Thalidomide on Transplantable Mouse, Rat, and Hamster Tumors", *GANN*, vol. 55, pp. 57–60 (1964).

Suzuki, H, "The History of Iatrogenic Diseases in Japan", *First Department of Internal Medicine, University of Envir. And Occup. Health, Kitakyushu, Japan*, pp. 35–40, Date not available.

Swift, T.R., "Thalidomide in Erythema Nodosum Leprosum", *Lancet*, vol. 2, No. 835, p. 966 (1973).

Szydlowska, et al., "On the Application of Thalidomide as a Block of Functional Groups of Proteins in Histochemical Investigations", *Folia Histo. Cytochem.*, vol. 16, No. 3, pp. 233–240 (1978).

Tamura, et al., "Combination Thalidomide and Cyclosporine for Cardiac Allograft Rejection. Comparison with Combination Methylprodnisolone and Cyclosporine", *Transplantation*, vol. 49, No. 1, pp. 20–25 (1990).

Taylor, S. et al., "Protamine is an Inhibitor of Angiogenesis", *Nature*, vol. 297, pp. 307–312 (1982).

Teppo, L. et al., "Thalidomide–Type Malformations and Subsequent Osteosarcoma", *The Lancet*, vol. II, No. 8034, p. 405 (1977).

"Thalidomide 20 Years On", *The Lancet*, vol. II, No. 8245, pp. 510–511 (1981).

"Thalidomide", *The Merck Index*, 11th ed., p. 1458 (1989).

Theophilus, S., "Treatment with Thalidomide in Steroid Dependency and Neuritis", *Lepr. India*, vol. 52, No. 3, pp. 423–428 (1980).

Thomas, et al., "Effect of Thalidomide on Liver Regeneration in Rat", *Indian J. Exp. Biol.*, vol. 10, pp. 314–315 (1972).

Thomas, et al., "Lack of Thalidomide Induced Aplasia in Regenerating Tail of Lizard, Hemidactylus Flavivirdis", *Indian J. Exp. Biol.*, vol. 10, pp. 316–317 (1972).

Thomas, L. et al., "Successful Treatment of Adult's Langerhans Cell Histiocytosis with Thalidomide", *Archives of Dermatol.*, vol. 129, pp. 1261–1264 (1993).

Torry, R. J. et al., "Angiogenesis in the Uterus: Potential Regulation and Relation to Tumor Angiogenesis", *Am. J. of Reproductive Immunology*, vol. 27, pp. 171–179 (1992).

Traldi, et al., "L'impiego Dell'imide Dell'Acido N'ftalilglutammico (Talidomide) Nella Terapia Sintomatica del Vomito di Molti Pazienti Affeti da Neoplasie Maligne o Causato Dalla Somministrazione di Cloridato di Mecloretamina", *Cancro*, vol. 18, pp. 336–341 (1965).

Trautman, J. R., "Treatment of Hansen's Disease", *Cutis*, vol. 18, No. 1, 62–65 (1976).

Van den Broek, H., "Treatment of Prurigo Nodularis with Thalidomide", *Arch. Dermatol*, vol. 116, No. 5, pp. 571–572 (1980).

Vasilescu, et al., "Cercetari Privind Actiunea Talidomidei Asupra Celulelor Cultivate in Vitro", *Cerc. Fiziol.*, vol. 13, No. 4, pp. 293–300 (1968).

Verhaul, et al., "Combination Oral Antiangiogenic Therapy with Thalidomide and Sulindac Inhibits Tumor Growth in Rabbits", *Brit. J. Cancer*, vol. 79, No. 1, pp. 114–118 (1999).

Vicente, T. et al., "In Vitro Activity of Thalidomide Against Mycobacterium avium Complex", *Archives of Internal Medicine*, vol. 153, p. 334 (1993).

Villa, et al., "Antimytotic Effect of Thalidomide and its Metabolites on the Chick Embryo Blood Cells", *Haematol. Latina*, vol. 6, pp. 217–221 (1963).

Villa, et al., "Cytological Effects of Thalidomide", *The Lancet*, p. 725 (1963).

Vladutiu, A., "Another Chance for Thalidomide?", *The Lancet*, vol. I, No. 7444, pp. 981–982 (1966).

Vogelsang, G. B. et al., "Thalidomide for the Treatment of Chronic Graft–Versus–Host Disease", *New England J. of Med.*, vol. 326, pp. 1055–1059 (1992).

Vogelsang, et al., "Therapy of Chronic Graft–v–Host Disease in a Rat Model", *Blood*, vol. 74, No. 1, No. 1, pp. 507–511 (1989).

Vogelsang, et al., "Thalidomide Induction of Bone Marrow Transplantation Tolerance", *Transplant Proc.*, vol. 19, No. 1, Pt. 3, pp. 2658–2661 (1987).

Vogelsang, et al., "Treatment and Prevention of Acute Graft–versus–Host Disease with Thalidomide in a Rat Model", *Transplantation*, vol. 41, No. 5, pp. 644–647 (1986).

Vogt, B. et al., "Inhibition of Angiogenesis in Kaposi's Sarcoma by Captopril", *The Lancet*, vol. 349, p. 1148 (1997).

Waters, M.F. et al., "Treatment of Ulcerative Colitis with Thalidomide", *Brit. Med. J.*, vol. 1, No. 6166, p. 792 (1979)

Waters, M.F., "An Internally–Controlled Double Blind Trial of Thalidomide in Severe Erythema Nodosum Leprosum ", *Lepro. Rev.*, vol. 42, No. 1, pp. 26–42 (1971).

Weidner, J. et al., "Tumor Angiogenesis and Metastasis–Correlation in Invasive Breast Carcinoma", *The New England J. of Med.*, vol. 324, No. 1, pp. 1–8 (1991).

Weidner, N. et al., "Tumor Angiogenesis Correlates with Metastasis in Invasive Prostate Cancer", *Am. J. of Pathol.*, vol. 143, No. 2, pp. 401–409 (1993).

Weidner, N. et al., "Tumor Angiogenesis: A New Significant and Independent Prognostic Indicator in Early–Stage Breast Carcinoma", *J. of Nat. Canc. Inst.*, vol. 84, No. 24, 1875–1887 (1992).

White, C. W. et al., "Treatment of Pulmonary Hemagiomatosis with Recombinant Interferon Alfa–2a", *The New England J. of Med.*, vol. 32, No. 18, pp. 1197–1200 (1989).

Williams, K. M., "Enantiomers in Arthritic Disorders", *Pharmacol. & Therapeutics*, vol. 46, No. 2, pp. 273–295 (1990).

Williams, et al., "Thalidomide Hypersensitivity in AIDS", *Lancet*, vol. 337, pp. 436–437 (1991).

Winkelmann, et al., "Thalidomide Treatment of Prurigo Nodularis", *Acta. Derm. Venereol.*, vol. 64, No. 5, pp. 412–417 (1984).

Wood, et al., "The Potential use of Thalidomide in the Therapy of Graft–versus–Host Disease –A Review of Clinical and Laboratory Information", *Leuk. Res.* , vol. 14, No. 5, pp. 395–399 (1990).

Woodyatt, P.B., "Thalidomide", *The Lancet*, p. 750. (1962).

Wulff, et al., "Development of Polyneuropathy During Thalidomide Therapy", *Br. J. Dermatol.*, vol. 112, No. 4, pp. 475–480 (1985).

Yazici, et al., "Practical Treatment Recommendations for Pharmacotherapy of Behcet's Syndrome", *Drugs*, vol. 42, No. 5, pp. 796–804 (1991).

Yoshimura, T. et al., "Cloning, Sequencing, and Expression of Human Macrophage Stimulating Protein (MSP, MST1) Confirms MSP as a Member of the Family of Kringle Proteins and Locates the MSP Gene on Chromosome 3", *The J. of Biol. Chem.*, vol. 268, No. 21, pp. 15461–15468 (1993).

Youle, et al., "Treatment of Resistant Aphthous Ulceration with Thalidomide in Patients Positive for HIV Antibody", *BMJ*, vol. 298, No. 6671, p. 432 (1989).

Youle, et al., "Thalidomide in Hyperalgic Pharyngeal Ulceration of AIDS", *Lancet*, vol. 335, No. 8705, p. 1591 (1990).

Yue, t. et al., "2–Methoxyestradiol, and Endogenous Estrogen Metabolite, Induces Apoptosis in Endothelial Cells and Inhibits Angiogenesis: Possible Role for Stress–Activated Protein Kinase Signaling Pathway and Fas Expression", *Molecular Pharmacology*, vol. 51, pp. 951–962 (1997).

Ziche, M. et al., "Nitric Oxide Synthase Lies Downstream from Vascular Endothelial Growth Factor–induced but Not Basic Fibroblast Growth Factor–Induced Angiogenesis", *J. Clin. Invest.*, vol. 99, No. 11, pp. 2625–2634 (1997).

Zwart, D., "Treatment of Grade II Astrocytoma with Thalidomide", *Arzneim..–Forsch.*, vol. 16, No. 12, pp. 1688–1689 (1966).

\* cited by examiner

US 6,673,828 B1

ANALOGS OF 2-PHTHALIMIDINOGLUTARIC ACID

CROSS REFERENCE TO RELATED APPLICATIONS

This application claims priority to U.S. Provisional Patent Application No. 60/085,037, filed on May 11, 1998, U.S. Provisional Patent Application No. 60/097,384, filed on Aug. 21, 1998, and U.S. Provisional Patent Application No. 60/108,037, filed on Nov. 12, 1998.

FIELD OF THE INVENTION

This invention is related to derivatives 2-methyl glutamic acid, namely 2-methyl-2-phthalimidinoglutaric acid and hydroxylated derivatives of 2-phthalimidinoglutaric. More particularly, the invention relates to the preparation of analogs of 2-phthalimidinoglutaric acid and the separation of the enantiomers of 2-methyl-2-phthalimidinoglutaric acid. Further, the invention relates to the use of such compounds for the treatment of cancer and for the treatment of angiogenesis-associated diseases.

BACKGROUND OF THE INVENTION

Angiogenesis is the generation of new blood vessels into a tissue or organ. Under normal physiological conditions, humans and animals undergo angiogenesis only in very specific, restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases is related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels, then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in many disease states, tumor metastases, and abnormal growth by endothelial cells. The diverse pathological disease states in which unregulated angiogenesis is present have been grouped together as angiogenic-dependent or angiogenic-associated diseases.

One example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens disease, acne rosacea, phylectenulosis, syphilis, Mycobacteria infections, lipid degeneration, chemical burns, bacterial ulcers, fungal ulcers, *Herpes simplex* infection, *Herpes zoster* infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with retinal/choroidal neovascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, lyme's disease, systemic lupus erythematosis, retinopathy of prematurity, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and postlaser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the bone destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels and the inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J. Med.*, 285:1182–86 (1971)). In its simplest terms, this hypothesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.*, 6:73–85 (1945)).

(2) Tumors grown in isolated perfused organs where blood vessels do not proliferate are limited to 1–2 mm$^3$ but expand rapidly to >1000 times this volume when they are transplanted to mice and become neovascularized. (Folkman, et al., *Annals of Surgery*, 164:491–502 (1966)).

(3) Tumor growth in the avascular cornea proceeds slowly and at a linear rate, but switches to exponential growth after neovascularization. (Gimbrone, Jr., et al., *J. Nat. Cancer Inst.*, 52:421–27 (1974)).

(4) Tumors suspended in the aqueous fluid of the anterior chamber of the rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et al., *J. Exp. Med.*, 136:261–76).

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347–56 (1977)).

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334–40 (1970)).

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman, et al., *Nature*, 339:58–61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature*, 362:841–44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180–84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross, et al., *Proc. Am. Assoc. Cancer Res.*, 31:79 (1990)).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555–57 (1990)). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner, et al., *New Eng. J. Med.*, 324:1–8 (1991); Weidner, et al., *J Nat. Cancer Inst.*, 84:1875–87 (1992)) and in prostate cancer (Weidner, et al., *Am. J. Pathol.*, 143(2): 401–09 (1993)) correlates highly with risk of future metastasis.

(15) Metastasis from human cutaneous melanoma is rare prior to neovascularization. The onset of neovascularization leads to increased thickness of the lesion and an increased risk of metastasis. (Srivastava, et al., *Am. J. Pathol.*, 133:419–23 (1988)).

(16) In bladder cancer, the urinary level of an angiogenic protein, bFGF, is a more sensitive indicator of status and extent of disease than is cytology. (Nguyen, et al., *J. Nat. Cancer Inst.*, 85:241–42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukemia-like tumors.

One of the most frequent angiogenic diseases of childhood is the hemangioma. A hemangioma is a tumor composed of newly-formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method which can inhibit angiogenesis. What is also needed is a composition and method which can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al. (*Nature*, 297:307 (1982)) have used protamine to inhibit angiogenesis. The toxicity of protamine limits its practical use as a therapeutic. Folkman, et al. (*Science*, 221:719 (1983), and U.S. Pat. Nos. 5,001,116 and 4,994,443) have disclosed the use of heparin and steroids to control angiogenesis. Steroids, such as tetrahydrocortisol, which lack gluccocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.*, 47:5155–61 (1987)). Human recombinant interferon (alpha/A) was reported to be successfully used in the treatment of pulmonary hemangiomatosis, an angiogenesis-induced disease. (White, et al., *New Eng. J. Med.*, 320:1197–1200 (1989)).

Other agents which have been used to inhibit angiogenesis include ascorbic acid ethers and related compounds. (Japanese Kokai Tokkyo Koho No.58-13 (1978)). Sulfated polysaccharide DS 4152 also inhibits angiogenesis. (Japanese Kokai Tokkyo Koho No. 63-119500). Additional anti-angiogenic compounds include Angiostatin® (U.S. Pat. Nos. 5,639,725; 5,792,845; 5,885,795; 5,733,876; 5,776,704; 5,837,682; 5,861,372, and 5,854,221) and Endostatin™ (U.S. Pat. No. 5,854,205).

Another compound which has been shown to inhibit angiogenesis is thalidomide. (D'Amato, et al., *Proc. Natl. Acad. Sci.*, 90:4082–85 (1994)). Thalidomide is a hypnosedative that has been successfully used to treat a number of angiogenesis-associated diseases, such as rheumatoid arthritis (Gutierrez-Rodriguez, *Arthritis Rheum.*, 27 (10):1118–21 (1984); Gutierrez-Rodriguez, et al., *J. Rheumatol.*, 16(2): 158–63 (1989)), Behcet's disease (Handley, et al., *Br. J. Dermatol.*, 127 Suppl, 40:67–8 (1992); Gunzler, *Med. Hypotheses*, 30(2):105–9 (1989)), graft versus host rejection (Field, et al., *Nature*, 211(55): 1308–10 (1966); Heney, et al., *Br. J. Haematol.*, 78 (1):23–7 (1991)), Mycobacteria diseases (Vicente, et al., *Arch. Intern. Med.*, 153(4):534 (1993)), *Herpes simplex* and *Herpes zoster* infections (Naafs, et al., *Int. J. Dermatol.*, 24(2):131–4 (1985)), chronic inflammation, ulcerative colitis (Meza, et al., *Drug Ther*, 23 (11): 74–80, 83 (1993); Powell, et al., *Br. J. Dermatol.*, 113 Suppl 28: 141–4 (1985)), leprosy (Barnes, et al., *Infect. Immun.*, 60(4):1441–46 (1992)) and lupus (Burrows, *BMJ*, 307: 939–40 (1993)).

Although thalidomide has minimal side effects in adults, it is a potent teratogen. Thus, there are concerns regarding its use in women of child-bearing age. Although minimal, there are a number of side effects which limit the desirability of thalidomide as a treatment. One such side effect is drowsiness. In a number of therapeutic studies, the initial dosage of thalidomide had to be reduced because patients became lethargic and had difficulty functioning normally. Another side effect limiting the use of thalidomide is peripheral neuropathy, in which individuals suffer from numbness and disfunction in their extremities.

Thus, improved methods and compositions are needed that are easily administered and capable of inhibiting angiogenesis.

SUMMARY OF THE INVENTION

The present invention provides new derivatives to 2-methyl glutamic acid, which are analogs of 2-phthalimidinoglutaric acid. Specifically, the present invention provides a new compound, 2-methyl-2-phthalimidinoglutaric acid and a process for its production. The present invention also provides for the individual (R) and (S) enantiomers of DL-2-methyl-2-phthalimidinoglutaric acid and processes for separating the (R) and (S) enantiomers.

2-methyl-2-phthalinmidinoglutaric acid (2-Me-EM-138) is a derivative of 2-phthalimidinoglutaric acid (EM-138) which has been shown by the present inventors to inhibit angiogenesis. The invention also provides methods for inhibiting angiogenesis and for treating angiogenesis-associated diseases with DL-2-methyl-2-phthalimidinoglutaric acid and with each of the individual enantiomers, R-(+)-2-methyl-2-phthalimidinoglutaric acid and S-(-)-2-methyl-2-phthalimidinoglutaric acid.

Further, the invention provides for hydroxylated derivatives of 2-phthalimidinoglutaric and processes for the preparation of such derivatives. The invention also provides for pharmaceutical compositions containing these derivatives and for their use in inhibiting angiogenesis and treating angiogenesis associated diseases.

Therefore, it is an object of the present invention to provide the compound DL-2-methyl-2-phthalimidinoglutaric acid.

It is another object of the present invention to provide a facile and economic method for producing the compound DL-2-methyl-2-phthalirnidinoglutaric acid.

It is yet another object of the present invention to provide methods for separating the individual enantiomers of DL-2-methyl-2-phthalimidinoglutaric acid.

It is a further object of the present invention to provide the compounds (R)-(+)-2-methyl-2-phthalimidinoglutaric acid and (S)-(-)-2-methyl-2-phthalimidinoglutaric acid.

Yet another object of the present invention is to provide hydroxylated derivatives of 2-phthalimidinoglutaric acid.

It is another object of the present invention to provide a process for the preparation of hydroxylated analogs of 2-phthalimidinoglutaric acid.

It is an object of the invention to provide pharmaceutical compositions containing DL-2-methyl-2-phthalimidinoglutaric acid, (R)-(+)-2-methyl-2-phthalimidino-glutaric acid, or (S)-(-)-2-methyl-2-phthalimidinoglutaric acid as an active ingredient.

It is an object of the invention to provide pharmaceutical compositions containing hydroxylated analogs of 2-phthalimidinoglutaric acid as an active ingredient.

It is an object of the present invention to provide a safe and effective method for inhibiting angiogenesis in a human or animal.

It is a further object of the invention to provide a safe and effective method for inhibiting angiogenesis in a human or animal by administering analogs of 2-phthalimidinoglutaric acid.

It is a further object of the present invention to provide a safe and effective method for inhibiting angiogenesis in a human or animal by administering DL-2-methyl-2-phthalimidinoglutaric acid, (R)-(+)-2-methyl-2-phthalimidinoglutaric acid, or (S)-(−)-2-methyl-2-phthalimidinoglutaric acid.

It is a further object of the invention to provide a safe and effective method for inhibiting angiogenesis in a human or animal by administering hydroxylated analogs of 2-phthalimidinoglutaric acid.

It is another object of the present invention to provide a method for the treatment of cancer, more particularly for the treatment of solid and blood-borne tumors.

It is another object of the present invention to provide a method for the treatment of cancer, more particularly for the treatment of solid and blood-borne tumors, by administering analogs of 2-phthalimidinoglutaric acid.

It is another object of the present invention to provide a method for the treatment of cancer, more particularly for the treatment of solid and blood-borne tumors, by administering DL-2-methyl-2-phthalimidinoglutaric acid, (R)-(+)-2-methyl-2-phthalimidinoglutaric acid, or (S)-(−)-2-methyl-2-phthalimidinoglutaric acid.

It is another object of the present invention to provide a method for the treatment of cancer, more particularly for the treatment of solid and blood-borne tumors, by administering hydroxylated analogs of 2-phthalimidinoglutaric acid.

It is yet another object of the present invention to provide a method for treating ulcerative colitis, Crohn's disease, ulcers, Behcet's syndrome, Stevens-Johnson's disease, Mycobacteria infections, *Herpes simplex* infections, *Herpes zoster* infections, rheumatoid arthritis, osteoarthritis, lupus, lyme's disease, chronic inflammation, atherosclerosis, and hereditary diseases.

It is yet another object of the present invention to provide a method for treating ulcerative colitis, Crohn's disease, ulcers, Behcet's syndrome, Stevens-Johnson's disease, Mycobacteria infections, *Herpes simplex* infections, *Herpes zoster* infections, rheumatoid arthritis, osteoarthritis, lupus, lyme's disease, chronic inflammation, atherosclerosis, and hereditary diseases by administering analogs of 2-phthalimidinoglutaric acid.

It is yet another object of the present invention to provide a method for treating ulcerative colitis, Crohn's disease, ulcers, Behcet's syndrome, Stevens-Johnson's disease, Mycobacteria infections, *Herpes simplex* infections, *Herpes zoster* infections, rheumatoid arthritis, osteoarthritis, lupus, lyme's disease, chronic inflammation, atherosclerosis, and hereditary diseases by administering DL-2-methyl-2-phthalimidinoglutaric acid, (R)-(+)-2-methyl-2-phthalimidinoglutaric acid, or (S)-(−)-2-methyl-2-phthalimidinoglutaric acid.

It is yet another object of the present invention to provide a method for treating ulcerative colitis, Crohn's disease, ulcers, Behcet's syndrome, Stevens-Johnson's disease, Mycobacteria infections, *Herpes simplex* infections, *Herpes zoster* infections, rheumatoid arthritis, osteoarthritis, lupus, lyme's disease, chronic inflammation, atherosclerosis, and hereditary diseases by administering hydroxylated analogs of 2-phthalimidinoglutaric acid.

Further, the present invention provides for a method of controlling wound healing.

The present invention also provides for a method of controlling wound healing by administering analogs of 2-phthalimidinoglutaric acid.

Further, the present invention provides for a method of controlling wound healing by administering DL-2-methyl-2-phthalimidinoglutaric acid, (R)-(+)-2-methyl-2-phthalimidino-glutaric acid, or (S)-(−)-2-methyl-2-phthalimidinoglutaric acid.

Further, the present invention also provides for a method of controlling wound healing by administering hydroxylated analogs of 2-phthalirnidinoglutaric acid.

It is another object of the present invention to induce abortion.

It is yet another object of the present invention to induce abortion by administering analogs of 2-phthalimidinoglutaric acid.

Another object of the present invention is to induce abortion by administering DL-2-methyl-2-phthalimidinoglutaric acid, (R)-(+)-2-methyl-2-phthalimidinoglutaric acid, or (S)-(−)-2-methyl-2-phthalimidinoglutaric acid.

It is another object of the present invention to induce abortion by administering hydroxylated analogs of 2-phthalimidinoglutaric acid.

DETAILED DESCRIPTION OF THE PREFERRED EMBODIMENTS

Figure 1:
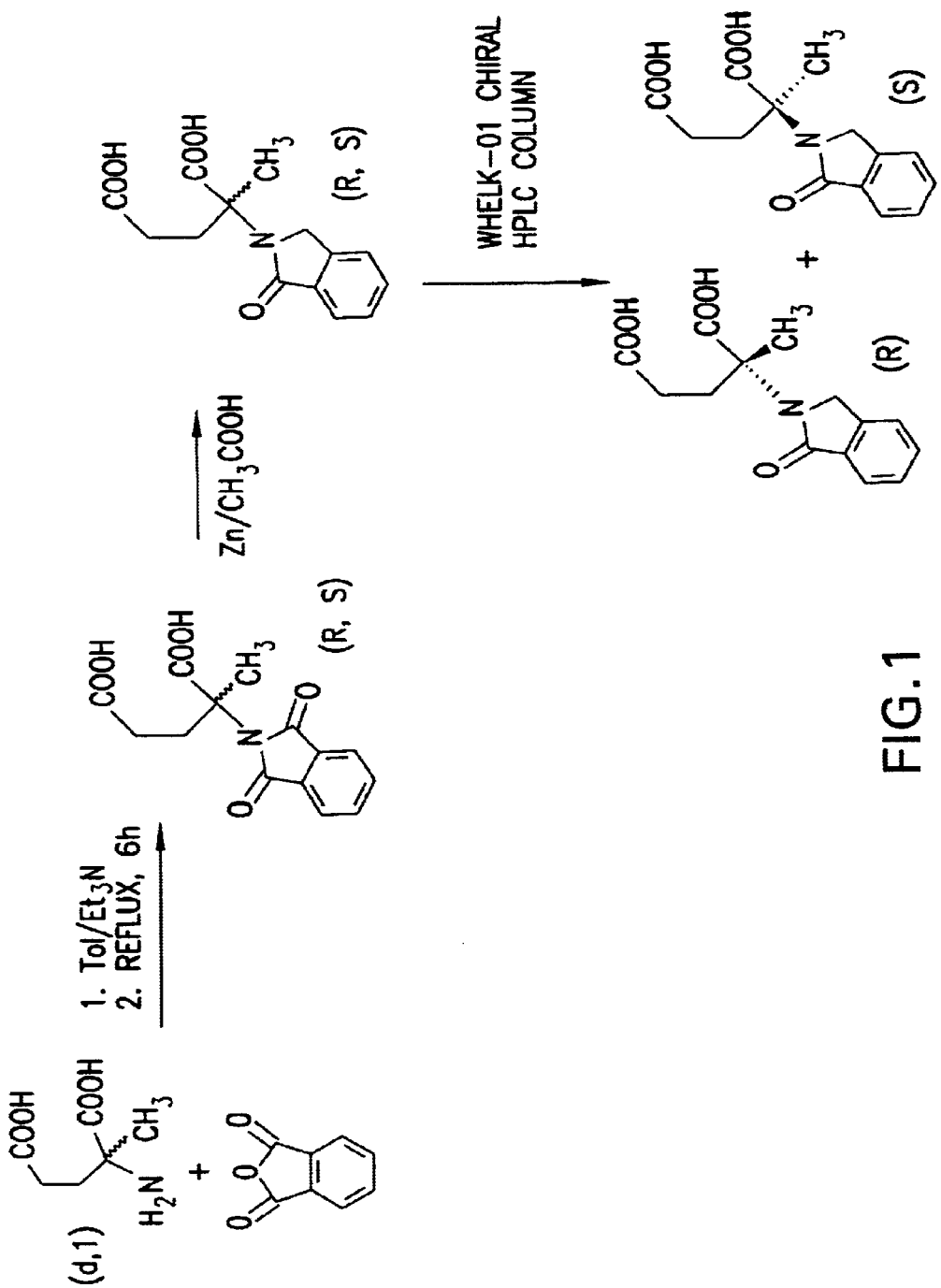
FIG. 1 depicts the synthesis of DL-2-methyl-2-phthalimidinoglutaric acid and separation of the (R) and (S) enantiomers by chiral HPLC.

The present invention provides that the compound 2-phthalimidinoglutaric acid (EM-138) has angiogenesis inhibitory activity and is useful for the treatment of a number of diseases, various cancers and macular degeneration. This compound has the following structure:

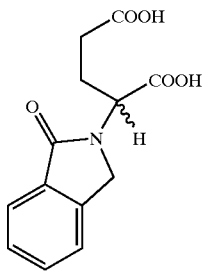

2-phthalimidinoglutaric acid (EM-138) is a stable, orally-active analog of thalidomide. Unlike thalidomide, it is relatively resistant to hydrolysis. It is a potent inhibitor of metastases. Even a single dose is capable of inhibiting metastasis by 50%, and a dose of 0.8 mmol/kg/day has been shown to inhibit metastasis by greater than 90%.

2-Methyl-2-phthalimidinoglutaric Acid

In the pharmaceutical arts, it is understood that one enantiomer of a compound often contains a significantly higher level of beneficial activity when compared to the other enantiomer. It has also been found that in some situations, one of the enantiomers provides beneficial effects while the other contributes to the toxicity or side effects of the drug.

It is not possible to separate EM-138 into its individual enantiomers because the enantiomers readily racemize. Therefore, the present inventors have synthesized a chiral compound related to EM-138 which has activity similar to that of EM-138 and can be separated into individual enantiomers. This compound is 2-methyl-2-phthalimidinoglutaric acid (2-Me-EM-138) and has the following structure:

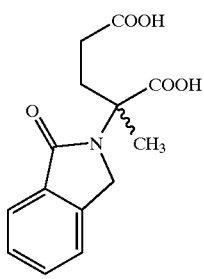

The compound may be synthesized in a number of ways. The preferred method of synthesis is from 2-methylglutamic acid. The 2-methylglutamic acid, phthalic anhydride, and an amine, such as triethyl amine, diethyl amine, or pyridine, are mixed in an anhydrous solvent, such as anhydrous toluene. The mixture is then heated under reflux followed by evaporation of the solvents. The intermediate, 2-methyl-N-phthaloylglutamic acid, is then crystallized and recovered.

The intermediate is then dissolved in acid, such as glacial acetic acid, followed by the addition of zinc dust. The mixture is then heated under reflux in an inert atmosphere, such as nitrogen or argon. The 2-methyl-2-phthalimidinoglutaric acid is then recovered and purified, for example, by recrystallization or elution on a silica gel column.

Studies of DL-2-methyl-2-phthalimidinoglutaric acid activity show that it is as potent an inhibitor of angiogenesis as EM-138. These studies indicate that the compound is useful for the treatment of angiogenesis-associated diseases. One angiogenesis-associated group of diseases is cancer. Numerous tumors, including solid tumors and blood-borne tumors, require angiogenesis to grow beyond a very small size. Inhibition of angiogenesis will result in inhibition of growth of the tumor. Examples of specific types of cancer which can be treated with 2-methyl-2-phthalimidinoglutaric acid and other derivatives encompassed by the present invention include, but are not limited to, prostate cancer, breast cancer, cervical cancer, uterine cancer, ovarian cancer, gliomas, hemangiomas, Kaposi's sarcoma, pancreatic cancer, retinoblastomas, melanomas, bladder cancer, rhabdomyosarcomas, retinoblastomas, Ewing's sarcoma, neuroblastomas, osteosarcoma, leukemia, and various acute and chronic neoplastic diseases of the bone marrow. The compound, 2-methyl-2-phthalimidinoglutaric acid, also inhibits metastases of existing tumors. Examples of metastases which can be inhibited include, but are not limited to, lung metastases, liver metastases, and peritoneal metastases.

Another group of angiogenesis-associated diseases occur in and around the eye. Examples of such eye diseases which can be treated with 2-methyl-2-phthalimidinoglutaric acid and other derivatives encompassed by the present invention include, but are not limited to, ocular neovascular disease, macular degeneration, including age-related macular degeneration, diabetic retinopathy, retinopathy of prematurity, corneal graph rejection, neovascular glaucoma, retrolental fibroplasia, epidemic keratoconjunctivitis, Vitamin A deficiency, contact lens overwear, atopic keratitis, superior limbic keratitis, pterygium keratitis sicca, Terrien's marginal degeneration, marginal ketatolysis, radial keratotomy, presumed ocular histoplasmosis, chronic uveitis/vitritis, myopia, optic pits, pars planitis, chronic retinal detachment, hyperviscosity syndromes, scleritis, trauma, post-laser complications, rubeosis, infections causing retinitis or choroiditis, and diseases caused by abnormal proliferations of fibrovascular or fibrous tissue, including all forms of prolific vitreoretinopathy.

A further group of angiogenesis-associated diseases are those characterized by tissue ulceration or breakdown. A number of these diseases also affect the eyes. Such diseases which can be treated with 2-methyl-2-phthalimidinoglutaric acid and other derivatives encompassed by the present invention include, but are not limited to, sjogrens disease, ulcerative colitis, Crohn's disease, Bartonelosis, acne rosacea, syphilis, sarcoidosis, chemical burns, bacterial ulcers, fungal ulcers, Behcet's syndrome, Stevens-Johnson's disease, Mycobacteria infections, *Herpes simplex* infections, *Herpes zoster* infections, protozoan infections, Mooren's ulcer, leprosy, Wegener's sarcoidosis, and pemphigoid. Other angiogenesis-associated diseases or disorders which can be treated with 2-methyl-2-phthalimidinoglutaric acid and other derivatives encompassed by the present invention include, but are not limited to, rheumatoid arthritis, osteoarthritis, lupus, systemic lupus erythematosis, polyarteritis, artery occlusion, vein occlusion, carotid obstructive disease, sickle cell anemia, pseudoxanthoma elasticum, Paget's disease, lyme's disease, Best's disease, Eale's disease, Stargardt's disease, toxoplasmosis, phylectenulosis, lipid degeneration, chronic inflammation, atherosclerosis, hereditary diseases, such as Osler-Weber-Rendu disease. The present compound can also be used to control wound healing by inhibiting the formation of adhesions and scars, to induce amenorrhea, and to induce abortion by blocking ovulation or preventing implantation of the blastula.

(R) and (S) Enantiomers of DL-2-Methyl-2-phthalimidinoglutaric Acid

In order to determine whether or not one of the enantiomers of DL-2-methyl-2-phthalimidinoglutaric acid has greater activity or reduced side effects, the enantiomers must first be separated. Separation may be accomplished by a number of different methods. In one preferred embodiment of the present invention, the enantiomers of DL-2-methyl-2-phthalimidinoglutaric acid are resolved by chiral high pressure liquid chromatography (HPLC) column. The sample is dissolved in an appropriate solvent and placed on the column. The sample is eluted then with a solvent mixture, such as a mixture of $CH_3CN/MeOH/H_2O/HOAc$ (1:1:5:0.1).

In another preferred embodiment, the enantiomers are separated by first forming an ester of DL-2-methyl-2-phthalimidinoglutaric acid. The ester may be produced by any known method. The particular ester formed is not critical. Nonlimniting examples of esters which can be formed include methyl esters, ethyl esters, propyl esters, and butyl esters. The dimethyl ester is preferred.

The esters are then separated using a hydrolysis agent which is enantiomerically specific, for example, ChiroCLEC™-BL. ChiroCLEC™-BL hydrolyzes one or both of the esters of only one of the enanatiomers, without affecting the other enantiomer. This enantiomerically-specific ester hydrolysis allows for the subsequent separation of the enantiomers using silica gel chromatography. Once separated, the esters are completely hydrolyzed to form the corresponding (R) and (S) acids. Hydrolysis may be performed in any manner. One preferred method of hydrolyzing the glutaric acid esters is by treatment with a 1:1 mixture of glacial acetic acid and concentrated hydrochloric acid.

Polarimetry has confirmed that the (R) enantiomer of 2-methyl-2-phthalimidinoglutaric acid rotates light in the (+) direction, while the (S) enantiomer rotates light in the (−) direction. Thus, the individual enantiomers of DL-2-methyl-2-phthalimidinoglutaric acid are (R)-(+)-2-methyl-2-phthalimidinoglutaric acid and (S)-(−)-2-methyl-2-phthalimidinoglutaric acid.

Hydroxylated Derivatives of 2-Phthalimidinoglutaric acid

The present inventors have also synthesized analogs of EM-138 containing hydroxyl groups on the benzene ring of the phthalimidino group. These compounds have the following structure:

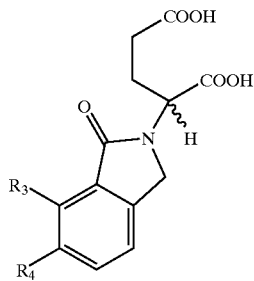

wherein each of $R_3$ and $R_4$ are independently H or OH.

These compounds may be synthesized in a number of ways. The preferred method of synthesis is from glutamic acid. Glutamic acid is reacted with phthalic anhydride or a derivative of phthalic anhydride under reflux in a solvent, such as pyridine, followed by the addition of diacetate to the reaction mixture. The intermediate produced is then hydrolyzed in an acid medium which opens the cyclic anhydride to form the glutaric acid derivative. The glutaric acid intermediate is then dissolved in acid, such as glacial acetic acid, followed by the addition of zinc dust.

Pharmaceutical Compositions and Methods of Administration

The compounds of the present invention may be administered orally, parenterally, rectally, vaginally, topically, transdermally, intravenously, intramuscularly, intraperatoneally, subcutaneously and the like. The dosage of the active compound will, of course, vary depending upon the subject to be treated, the particular disease or condition to be treated, the seriousness of the disease or condition, the route of administration, and the judgment of the prescribing practitioner. Determination of the dosage on the basis of such factors is within the level of ordinary skill in the art. In general, the dosage will range from approximately 100 mg/kg/day to approximately 2000 mg/kg/day.

The compounds of the present invention can be conveniently formulated into pharmaceutical compositions in association with a pharmaceutically acceptable carrier. Remington's Pharmaceutical Sciences, latest edition, by E. W. Martin (Merck Publ. Co., Easton, Pa.) discloses typical carriers and conventional methods of preparing pharmaceutical compositions which may be employed to prepare the compositions of the present invention. The compounds of the present invention can also be administered in conjunction with other active compounds, such as other anti-angiogenic agents.

Depending upon the intended mode of administration, the pharmaceutical compositions may be in the form of solid, semi-solid, or liquid dosage forms. Examples of dosage forms include, but are not limited to, tablets, pills, capsules, suppositories, sachets, granules, powders, creams, lotions, ointments, patches, liquid solutions, suspensions, and dispersions, emulsions, syrups, and the like. The active ingredient may also be encapsulated in liposomes, microparticles, or microcapsules, and the like.

Conventional nontoxic carriers include, but are not limited to, pharmaceutical grades of mannitol, lactose, starch, magnesium stearate, sodium saccharine, talc, cellulose, glucose, sucrose, dextrose, glycerol, magnesium carbonate, triglycerides, oils, solvents, sterile water, and isotonic saline. Solid compositions such as tablets, pills, granules, etc. may conveniently be coated. Typically, compositions for intravenous administration are solutions in sterile isotonic aqueous buffer and may include a local anesthetic to ameliorate pain at the injection site. If desired, the pharmaceutical may also contain minor amounts of nontoxic auxiliary substances, such as wetting agents, emulsifying agents, pH buffering agents, and the like. Examples of such auxiliary substances include, but are not limited to, sodium acetate, sorbitan monolaurate, triethanolamine, and triethanolamine oleate. The compositions of the present invention may also include such excipients as stabilizers, antioxidants, binders, coloring agents, flavoring agents, preservatives, and thickeners.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Examples 1

Inhibition of Metastasis Through Intraperitoneal Administration of EM-138

Figure 4:
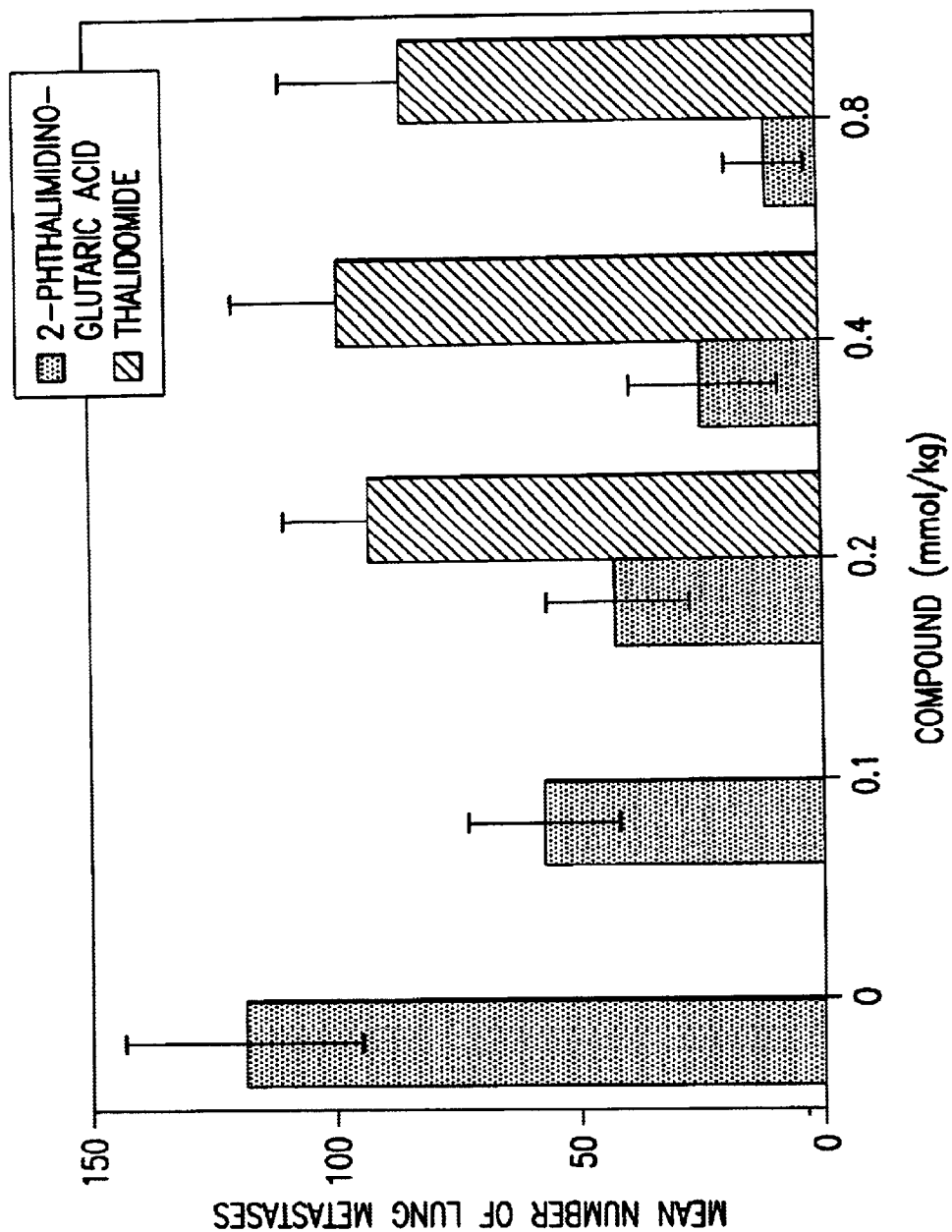
FIG. 4 shows the effect of EM-138 as compared to thalidomide administered intraperitoneally on the inhibition of metastasis in B16-BL6 melanoma cells.

B16-BL6 melanoma cells ($5 \times 10_4$) were injected intravenously into the tail veins of C57B1/6 mice. Three days later, the mice were treated intraperitoneally with increasing doses of thalidomide or 2-phthalimidinoglutaric acid (EM-138) on alternate days. Fourteen days after tumor cell inoculation, the lungs were removed from the mice and the surface pulmonary metastases were counted. The results of this experiment are shown in FIG. 4. The values shown are the mean of 5 mice per group. The bars on the graph represent the standard deviation.

Example 2

Inhibition of Metastasis Through Oral Administration of EM-138

Figure 5:
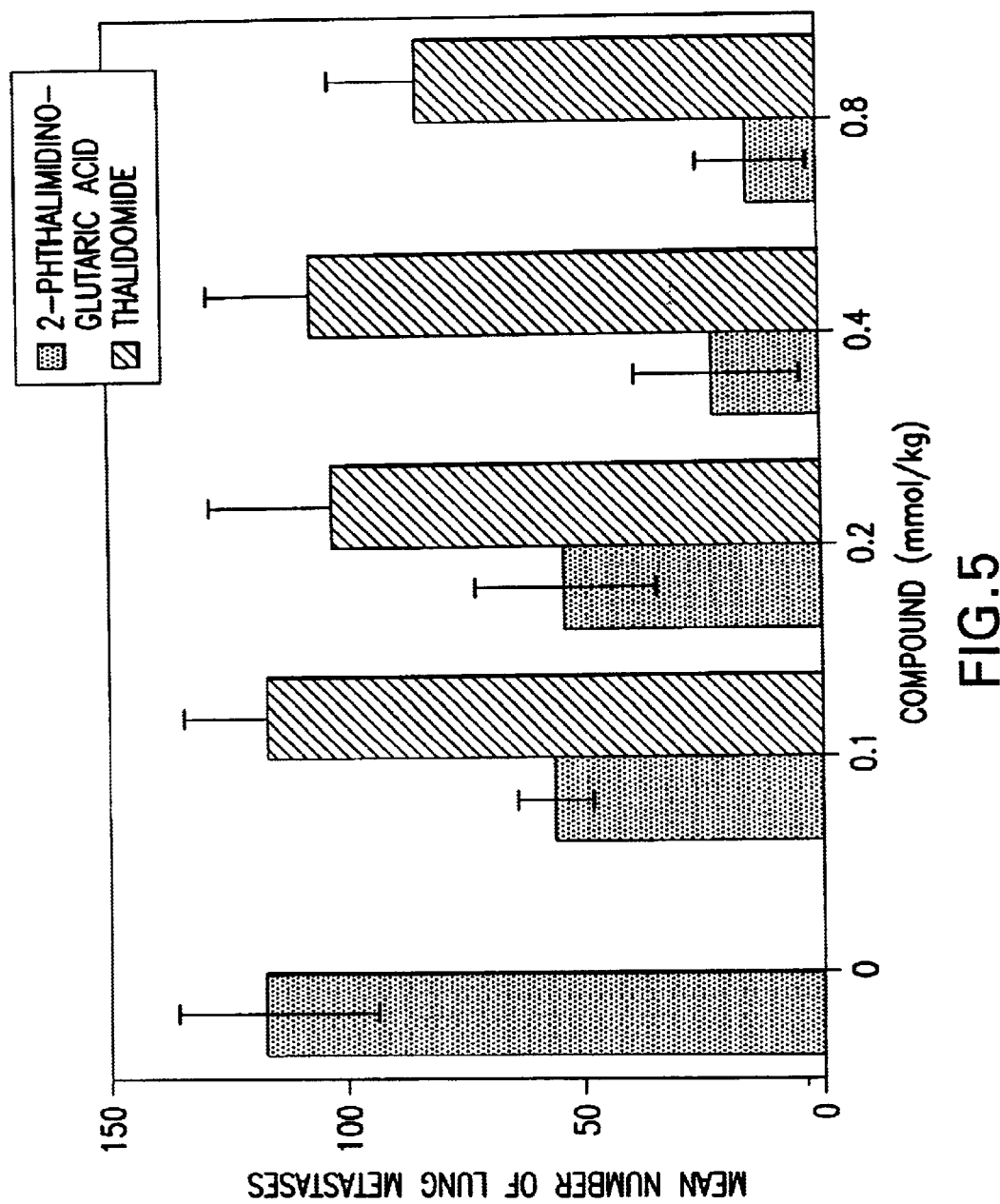
FIG. 5 shows the effect of EM-138 as compared to thalidomide administered orally on the inhibition of metastasis in B16-BL6 melanoma cells.

B16-BL6 melanoma cells ($5 \times 10_4$) were injected intravenously into the tail veins of C57Bl/6 mice. Three days later, the mice were treated orally with increasing doses of thalidomide or 2-phthalimidinoglutaric acid (EM-138) on alternate days. Fourteen days after tumor cell inoculation, the lungs were removed from the mice and the surface pulmonary metastases were counted. The results of this experiment are shown in FIG. 5. The values shown are the mean of 5 mice per group. The bars on the graph represent the standard deviation.

Example 3

Effect of the Number of Treatments on EM-138 Activity

Figure 6:
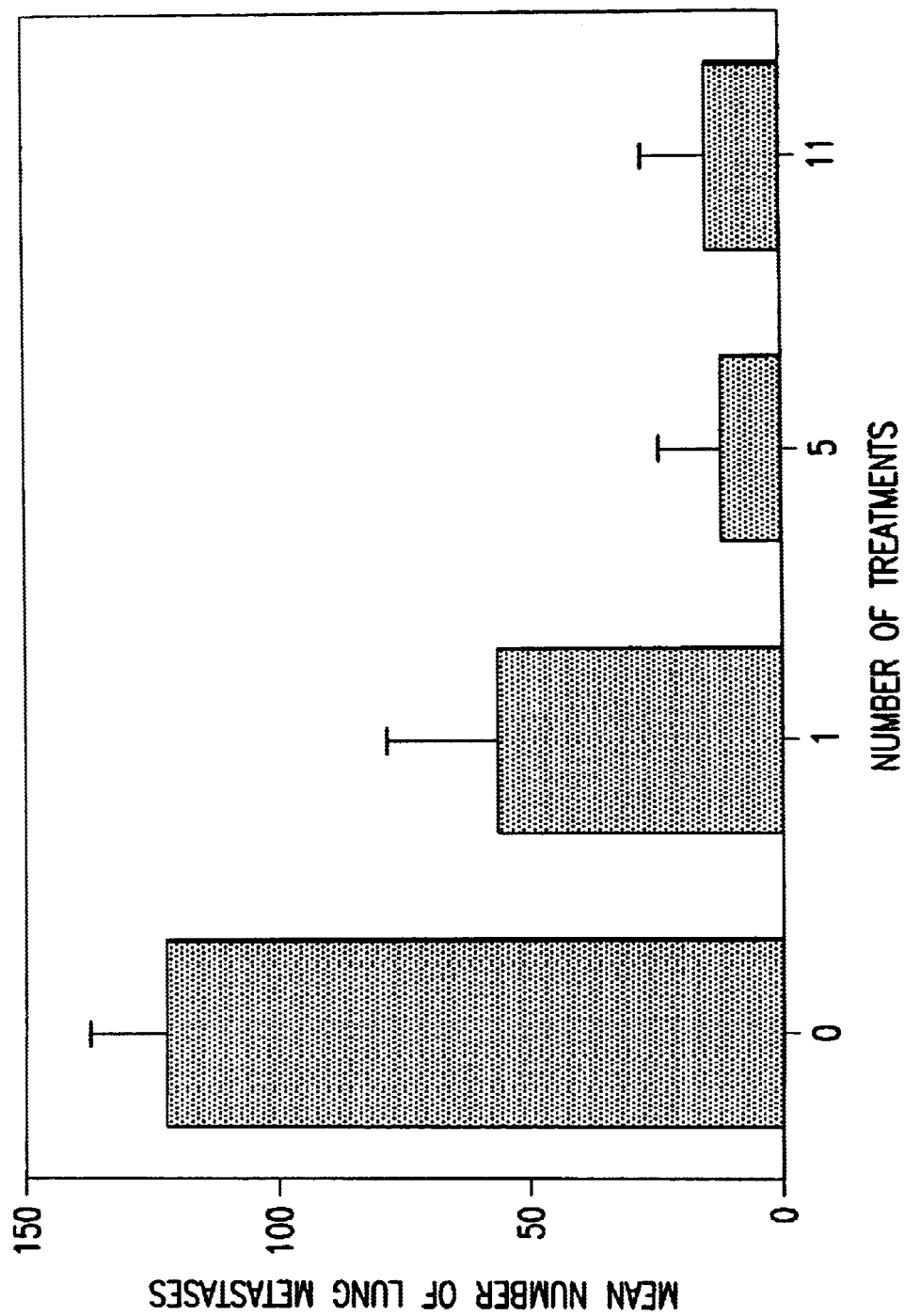
FIG. 6 shows the effect of the number of treatments on the activity of 2-phthalimidinoglutaric acid in the B16-BL6 model.

B16-BL6 melanoma cells ($5 \times 10_4$) were injected intravenously into the tail veins of C57Bl/6 mice. Three days later, the mice received a gavage treatment with 0.8 mmol/kg of 2-phthalimidinoglutaric acid (EM-138). The mice received either a single treatment, five treatments on alternate days, or one treatment every day for eleven days. Fourteen days after tumor cell inoculation, the lungs were removed from the mice and the surface pulmonary metastases were counted. The results of this experiment are shown in FIG. 6. The values shown are the mean of 5 mice per group. The bars on the graph represent the standard deviation.

Example 4

Effect of Initial Treatment Time of EM-138 Activity

Figure 7:
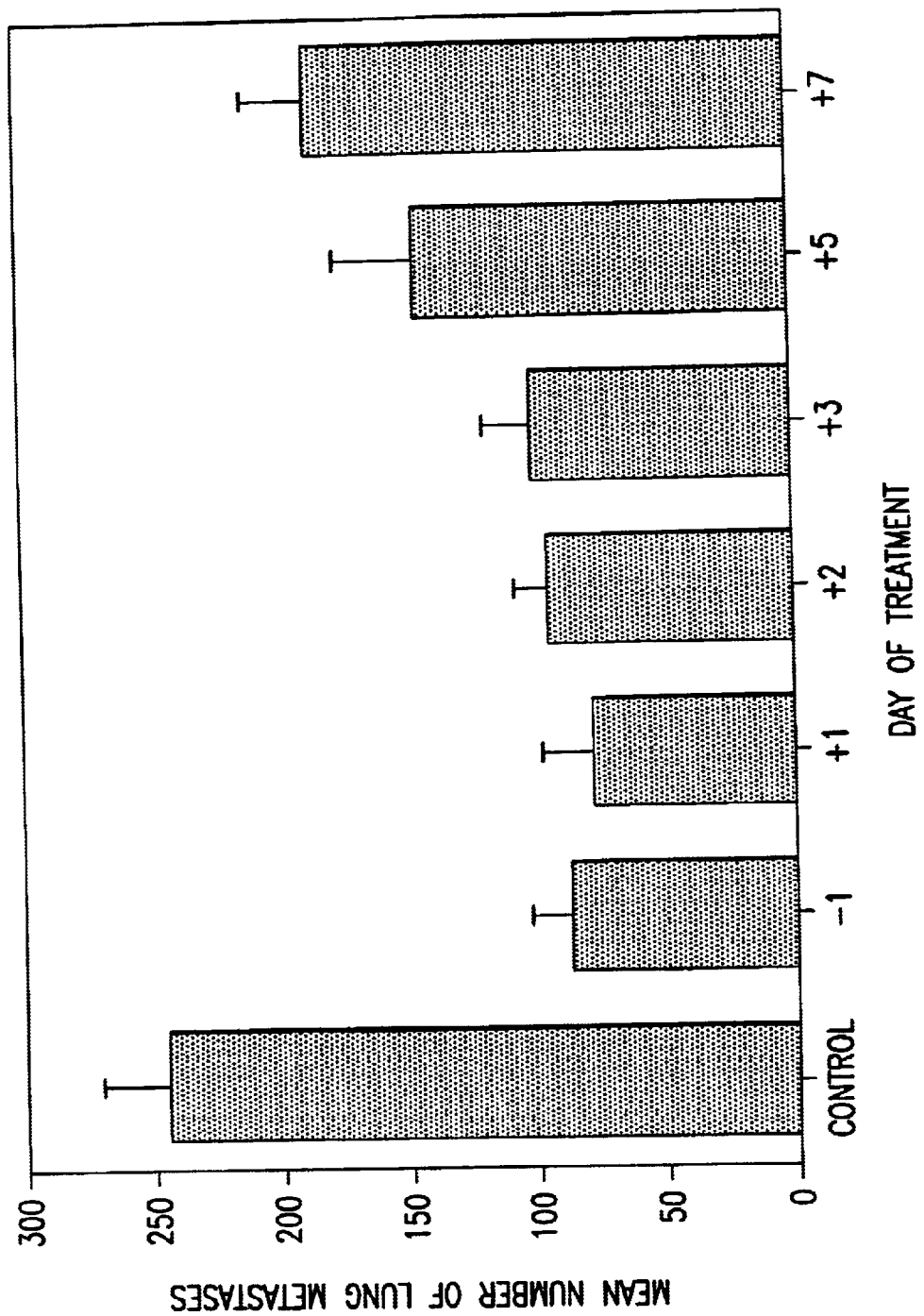
FIG. 7 shows the effect of initial treatment time on EM-138 activity in B16/BL6 melanoma cells.

B16-BL6 melanoma cells ($5 \times 10_4$) were injected intravenously into the tail veins of C57B 1/6 mice. The mice were given a single oral treatment of 2-phthalimidinoglutaric acid (EM-138) of 0.8 mmol/kg. The treatment was initiated one day prior to tumor cells or on day 1, 2, 3, 5, or 7 after tumor cells. Fourteen days after tumor cell inoculation, the lungs were removed from the mice and the surface pulmonary metastases were counted. The results of this experiment are shown in FIG. 7. The values shown are the mean of 5 mice per group. The bars on the graph represent the standard deviation.

Example 5

Lung Macropathology in EM-138 Treated Mice

Figure 8:
FIG. 8 shows the lung macropathology of mice treated with 2-phthalimidinoglutaric acid (EM-138).

Mice with pulmonary B16-BL6 metastases were orally administered either 0.5% carboxymethylcellulose or 0.8 mmol/kg of 2-phthalimidinoglutaric acid (EM-138). The results of this experiment are show in FIG. 8 (0.5% carboxymethylcellulose (left panel) and 0.8 mmol/kg EM-138 (right panel).

Example 6

Lung Histopathology in EM-138 Treated Mice

Figure 9:
FIG. 9 shows the lung histopathology of mice treated with 2-phthalimidinoglutaric acid (EM-138).
Figure 10:
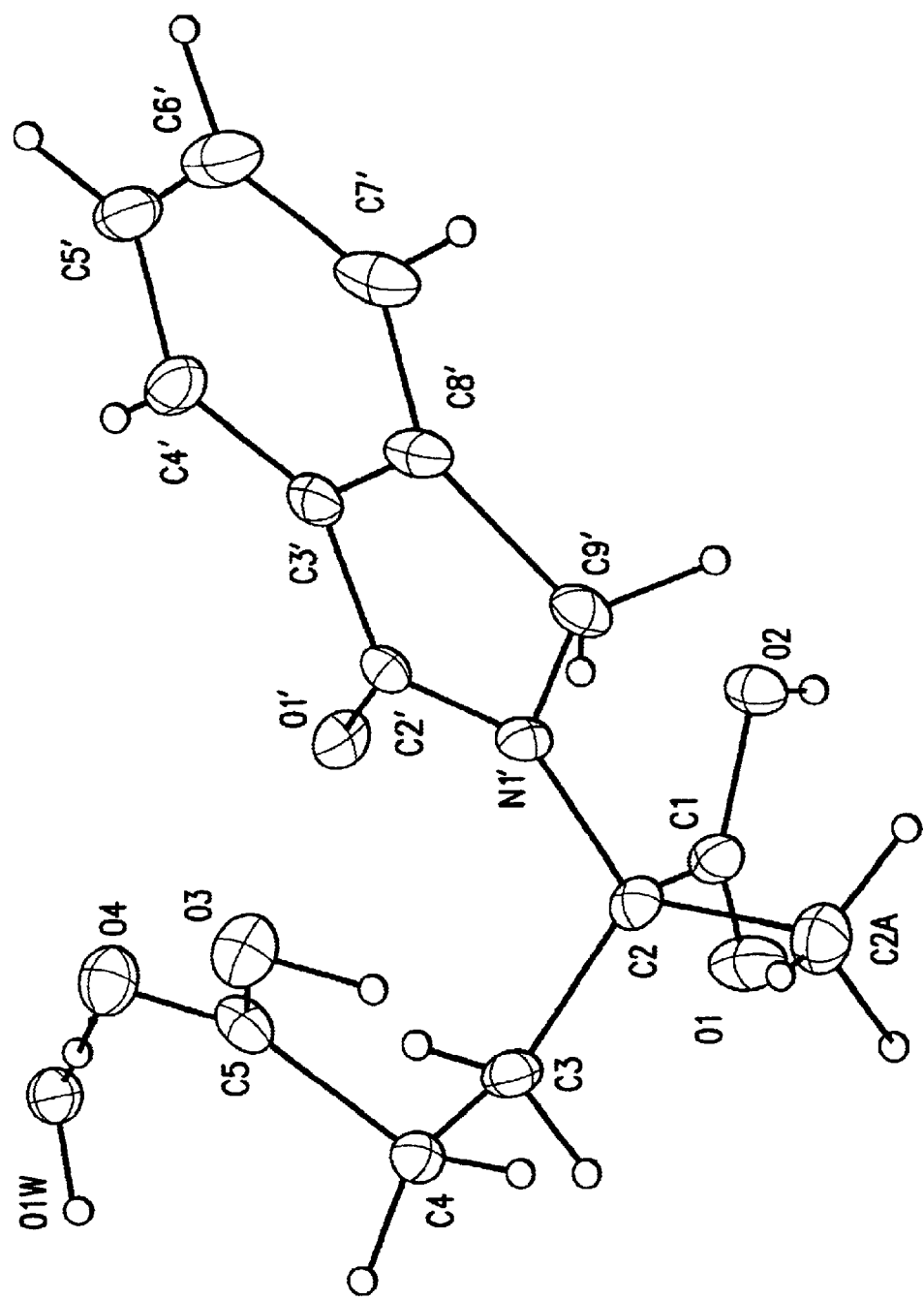
FIG. 10 depicts the crystalline structure of 2-methyl-2-phthalimidinoglutaric acid.
Figure 11:
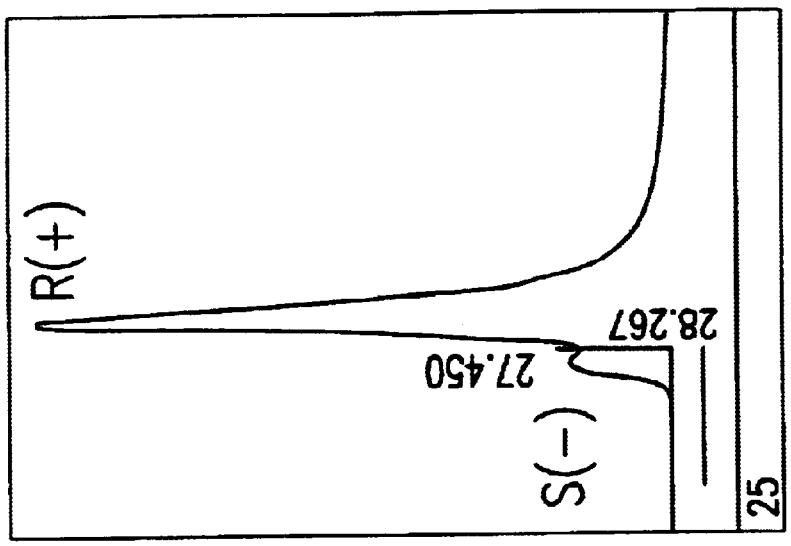
FIG. 11 shows the chiral resolution of the (R) and (S) enantiomers of DL-2-methyl-2-phthalimidinoglutaric acid by HPLC using $CH_3CN/MeOH/H_2O/HOAc$ (1:1:5:0.1) as the eluant at a flow rate of 2 ml/min at 230 nm.
Figure 11:
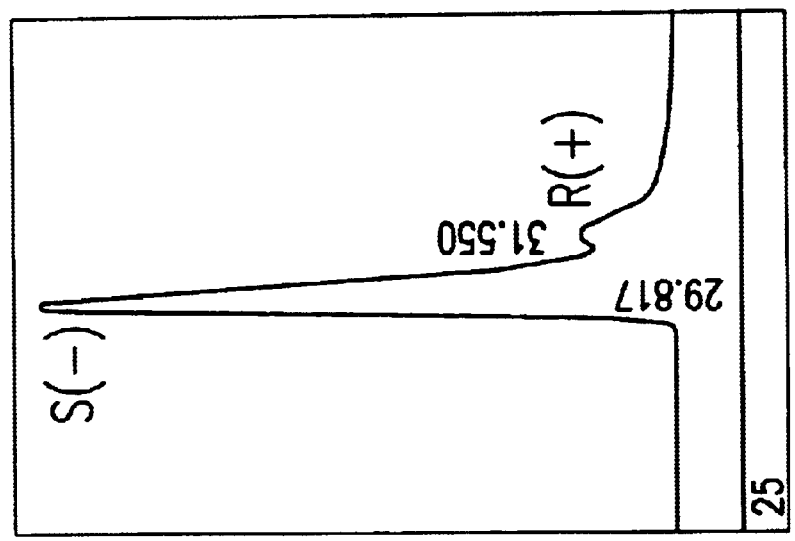
Figure 11:
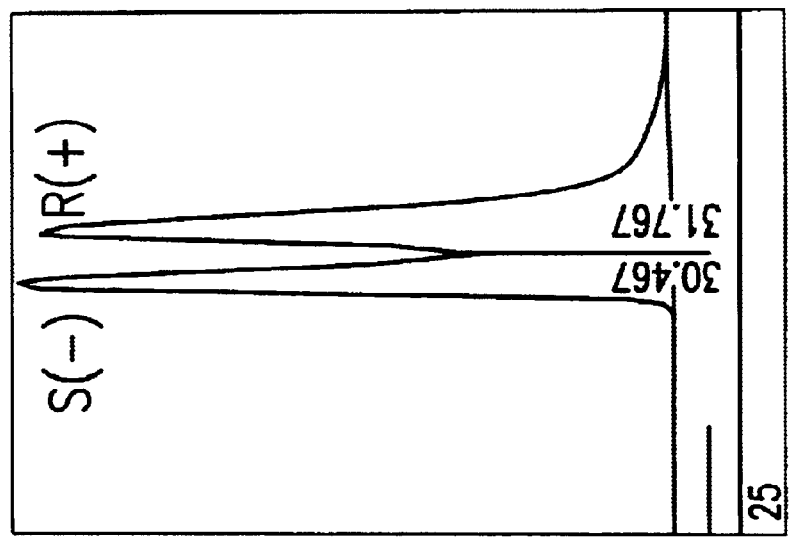
Figure 12:
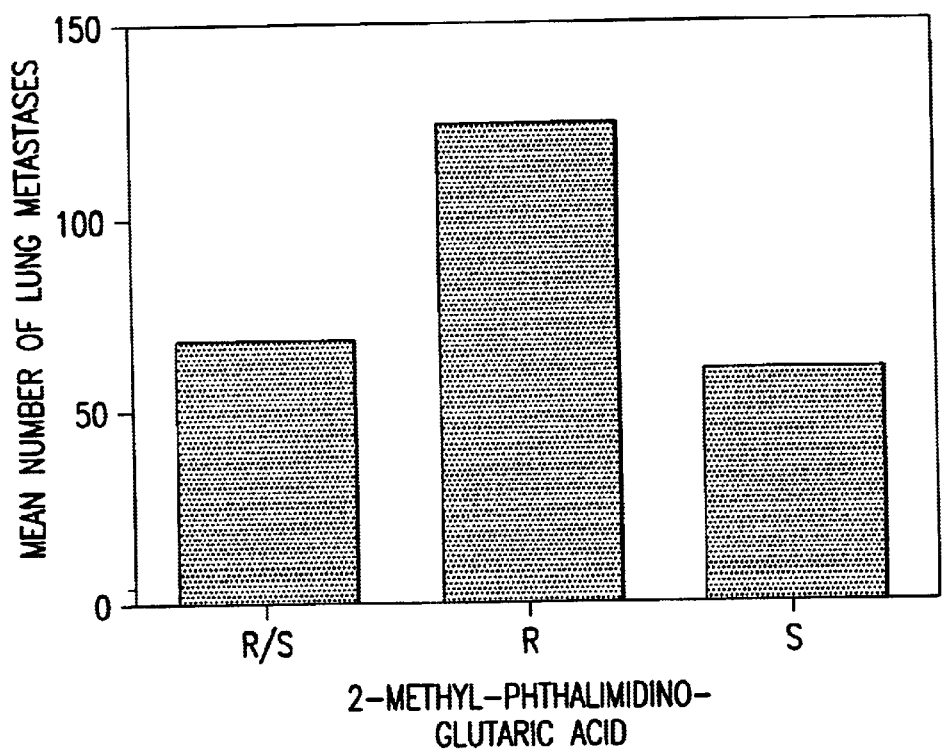
FIG. 12 shows the effect of optically-pure enantiomers of 2-methyl-2-phthalimidinoglutaric acid on B16-BL6 melanoma metastases.
Figure 13:
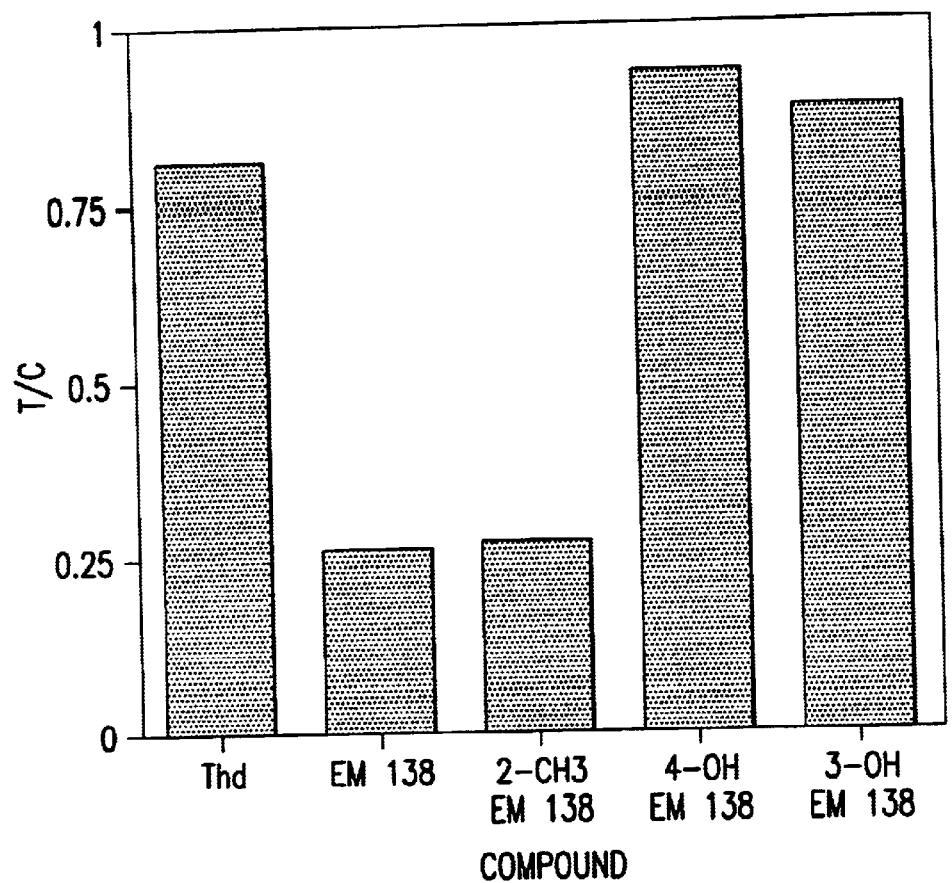
FIG. 13 shows the relative anti-tumor activity of thalidomide, EM-138, and analogs of EM-138. T/C is the ratio of tumors to control. Thus, the lower the T/C ratio the greater the tumor inhibitory activity of the compound.

Melanoma-bearing mice were treated orally with either 0.5% carboxymethylcellulose or 0.8 mmol/kg of 2-phthalimidinoglutaric acid (EM-138). The lungs of the mice were removed, fixed with formalin, and embedded in paraffin. Random sections from representative lungs from each group were stained with hematoxylin and eosin. The sections were photographed at 100×magnification. The results are shown in FIG. 9 ((0.5% carboxymethylcellulose (left panel) and 0.8 nmmol/kg EM-138 (right panel)).

Example 7

General Synthetic Procedure for 2-phthalimidino Glutaric Acid Analogs

Figure 3:
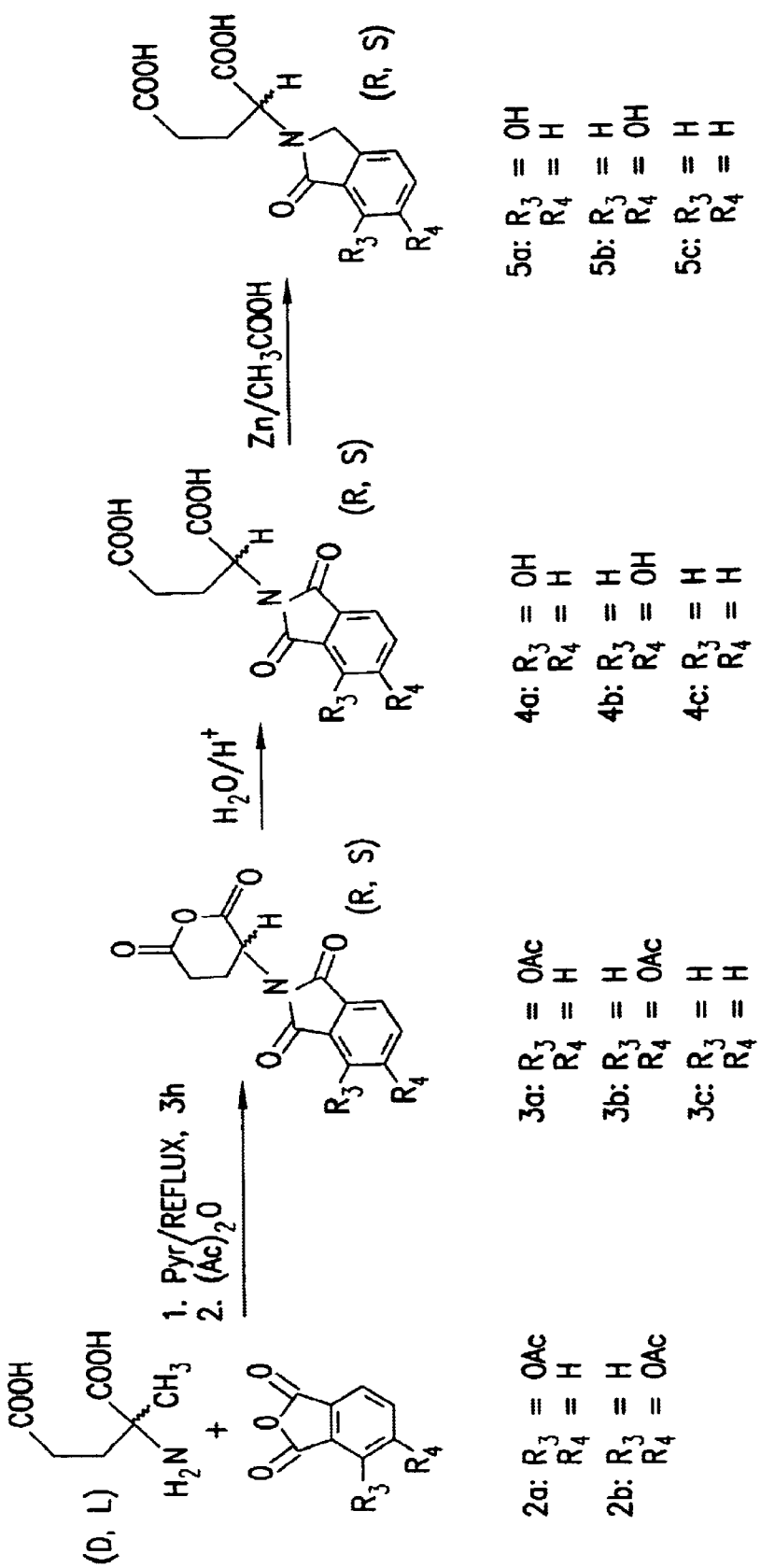
FIG. 3 depicts the synthesis of hydroxylated derivatives of 2-phthalimidinoglutaric.

Equimolar amounts of (dl)-glutamic acid and 3' and 4' substituted phthalic anhydrides were heated under reflux in anhydrous pyridine for 3–4 h. After completion of the coupling reaction, the pyridine was evaporated under reduced pressure and the viscous product is mixed with acetic anhydride (3 equivalents) and heated to boil for 10 minutes. Evaporation of approximately half of the volume of acetic anhydride and cooling of the reaction mixture at room temperature gave a white crystalline product that was separated by filtration to give substituted N-phthaloyl-dl-glutamic anhydride products (3a and 3b of FIG. 3) (60–75% yield).

The anhydrides (3a, 3b and 3c of FIG. 3) were hydrolyzed by boiling water, recrystallized and dried under vacuum to give the substituted phthaloyl (dl) glutamic acid products (4a, 4b and 4c of FIG. 3) in 98% yield. These products were partially reduced by treating with 5 equivalent Zn dust in acetic acid to afford the 2-phthalimidino glutaric acid analogs (5a, 5b and 5c in FIG. 3) in 60–80% yields.

Example 8

Preparation of DL-2-Methyl-N-phthaloylglutamic Acid

A mixture of vacuum dried DL-2-methylglutamic acid (6.8 gram, 40 mmol), phthalic anhydride (5.92 grams, 40 mmol), and 150 ml triethylamine in anhydrous toluene was heated under reflux using Dean-Stark apparatus. After 4 hours of heating, 0.7 ml water was collected. The reaction mixture was heated for an additional 2 hours and then the solvents were evaporated. On dissolving this reaction mixture in 40 ml 1N HCl solution, white crystals began to form. After 18 hours, the crystals were separated from the mother liquor by suction filtration and dried under vacuum to give 8.1 grams, (60%) white solid product. H1-NMR confirmed the product as DL-2-methyl-N-phthaloylglutamic acid.

Example 9

Preparation of DL-2-Methyl-2-phthalimidinoglutaric Acid

A 1.6 gram (4 mmol) portion of the DL-2-methyl-N-phthaloylglutamic acid prepared in Example 8 was dissolved in 10 ml glacial acetic acid. 1.3 gram (20 mmol) Zn dust was added to the reaction mixture. The reaction mixture was heated under reflux under a nitrogen atmosphere. After 4 hours of heating, silica gel TLC analysis ($CHCl_3$/MeOH 4:1) of reaction mixture showed formation of new product of higher Rf value. The reaction mixture was heated for an additional hour, and then the hot liquid was filtered by suction. After evaporating acetic acid under reduced pressure, the viscous product was dissolved in 5 ml water and impurities were removed by washing the water layer with ethyl ether. On standing, white crystals were formed in the water layer overnight which were then separated by suction filtration. The crystalline material was further purified by passing it through silica gel column and eluted with CHCl$_3$/MeOH (4:1) mixture to give viscous product. The product was then recrystallized from water and dried under vacuum to give 600 mg (60) white solid. 1H-NMR confirmed the product DL-2-methyl-2-phthalimidinoglutaric acid (JHS- 171). 1 H-NMR (DMSO-D6, PPM), 7.7 (3H, m), 7.5 (1H, d), 4.62 (2H, s), 3.4 (2H, broad), 2.46 (1H, d, t, J=11.5, 6.5), 2.3 (1H, t, J=9.5), 2.1 (2H, m), 1.46 (3H, s). (FIG. 1)

Example 10

Treatment of Pulmonary Metastasis by 2-Methyl-2-phthalimidinoglutaric Acid.

B16-BL6 melanoma cells (5×104) were injected intravenously into the tail veins of C57B 1/6 mice. The mice were given intraperitoneal (i.p.) treatments of either 1.0 ml 2.8% DMSO alone (control), 1.0 ml (5.0 mg/mi 2.8% DMSO) 2-phthalimidinoglutaric acid (EM-138) in DMSO, or 1.0 ml (5.0 mg/ml 2.8%) 2-methyl-2-phthalimidinoglutaric acid (2-Me-EM-138) in DMSO four times a day beginning 72 hours after injection of the tumor cells. Fourteen days after tumor cell inoculation, the lungs were removed from the mice and the surface pulmonary metastases were counted. The results of this experiment are shown in the following table.

| Treatment group | Mean Number of Pulmonary Metastases (range) | % Inhibition |
| --- | --- | --- |
| DMSO (n = 5) | 210 (164–261) | — |
| EM-138 (n = 5) | 85 (51–118) | 60% |
| 2-Me-EM-138 | 84 (1–124) | 60% | n = number of mice per sample group
p < 0.01, as compared to DMSO-treated control group

Example 11

Separation of 2-Methyl-EM-138 Enantiomers by HPLC

The two enantiomers of DL-2-methyl-2-phthalimidinoglutaric acid were resolved by chiral HPLC column. The compound DL-2-methyl-2-phthalimidinoglutaric acid in methanol was placed on a Welk-01 (10 mm×750 mm) and eluted with a CH$_3$CN/MeOH/H$_2$O/HOAc (1:1:5:0.1) mixture. The retention time for S (−) isomer was 25.96 minutes and for R (+) isomer 26 minutes at a flow rate 2 ml/min. Absorbance was monitored at 230 nanometers. (FIG. 1)

Example 12

Preparation of as DL-2-Methyl-2-phthalimindinoglutaric Acid Dimethyl Ester

Figure 2A:
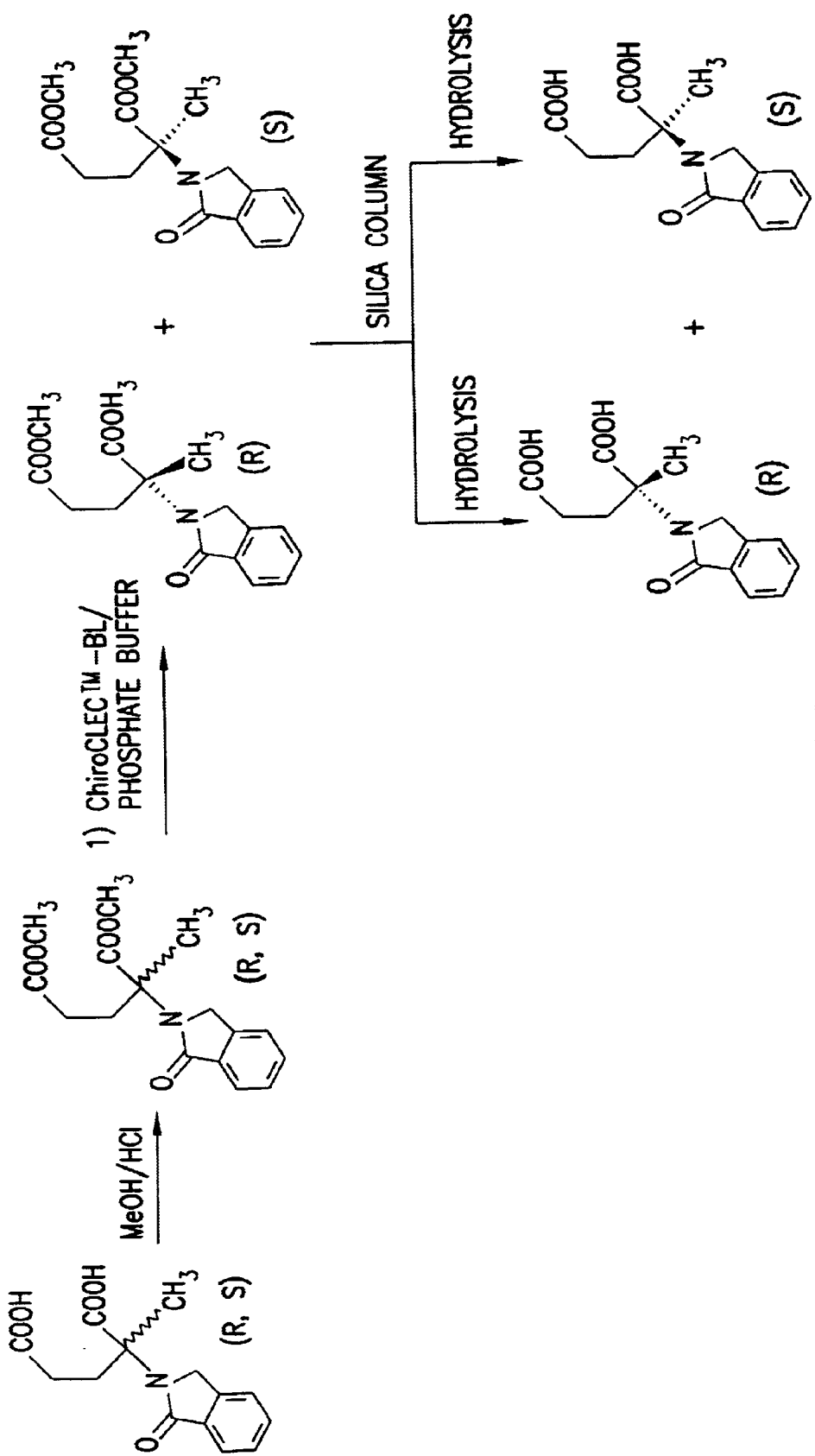
FIGS. 2a and 2b depict the synthesis of DL-2-methyl-2-phthalimidinoglutaric acid dimethyl ester, its separation of the (R) and (S) enantiomers using ChiroCLEC™-BL and hydrolysis to form (R)-(+)-2-methyl-2-phthalimidinoglutaric acid and (S)-(−)-2-methyl-2-phthalimidinoglutaric acid.
Figure 2B:
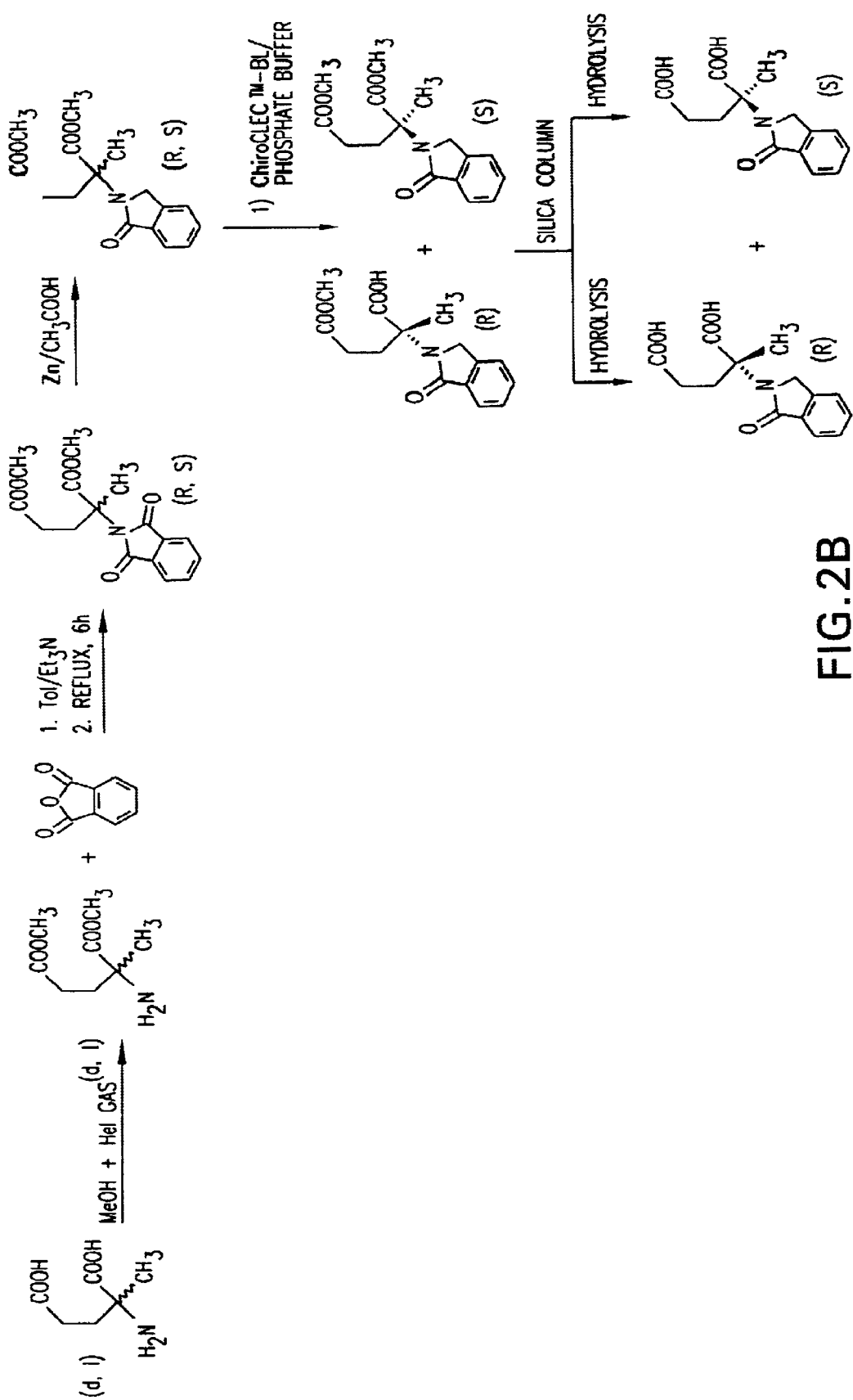

A 150 mg portion of DL-2-methyl-2-phthalimidinoglutaric acid was dissolved in 10 ml anhydrous methanol saturated with HCl gas and stirred for 30 minutes at 40–50° C. TLC analysis (CHCl$_3$/MeOH 95:5) of reaction mixture showed formation of new product of higher Rf value. After evaporating the solvents, the product is purified on a silica gel column and eluted with CHCl$_3$/MeOH (4:1) mixture to give viscous product (130 mg, 90%). 1H-NMR confirmed the product as DL-2-methyl-2-phthalimindinoglutaric acid dimethyl ester (JHS-2-7). (FIG. 2)

Example 13

Separation of the (R) and (S) Isomers of 2-Me-EM-138 by ChiroCLEC™-BL Catalyst

To a solution of 130 mg DL-2-methyl-2-phthalimidinoglutaric acid dimethyl ester in 2 ml acetone, was added 7.8 ml of 2.5 M, pH 8.5 phosphate buffer. ChiroCLEC™-BL (0.4 ml, 8 mg) suspension was added. The reaction mixture was heated for 18 hours at 40–50° C. TLC analysis (CHCl$_3$/MeOH 95:5) of reaction mixture showed formation of new product of lower Rf value than the starting material. After stirring 2 additional hours, 4 ml acetone was added and the catalyst was filtered by suction. After evaporating the solvents, 2 products were separated by silica gel column and eluted with CHCl$_3$/MeOH (98:2) mixture to give early eluting viscous product, JHS-2-13-P1 (70 mg, 90%), and late eluting product, JHS-2-13-P2 (40 mg, 70%). Analysis on a polarimeter of product JHS-2-13-P1 showed (+) rotation and of product JHS-2-13-P2 showed (−) rotation. 1H-NMR confirmed the product JHS-2-13-P1 as R-(+)-2-methyl-2-phthalimidinoglutaric acid dimethyl ester, and JHS-2-13-P2 as S-(−)-2-methyl-2-phthalimidinoglutaric acid monomethyl ester.

Products JHS-2-13-P1 and JHS-2-13-P2 were hydrolyzed by treating with 1:1 mixture of glacial acetic acid and conc. HCl for a period of 1 hour at 90–100° C. to give R-(+)-2-methyl-2-phthalimidinoglutaric acid (JHS-2-23-R) and S-(−)-2-methyl-2-phthalimidinoglutaric acid (JHS-2-23-S), respectively. (FIG. 2)

Example 14

Treatment of Pulmonary Metastasis by R-(+)-2-Methyl-2-phthalimidinoglutaric Acid and S(−)-2-Methyl-2-phthalimidinoglutaric Acid.

B16-BL6 melanoma cells (5×10$^4$) were injected intravenously into the tail veins of C57B1/6 mice. The mice were given intraperitoneal (i.p.) treatments of either 1.0 ml 2.8% DMSO alone (control), 1.0 ml (5.0 mg/ml) DL-2-methyl-2-phthalimnidinoglutaric acid (racemate) in 2.8% DMSO, 1.0 ml (5.0 mg/ml) (R)-(+)-2-methyl-2-phthalimidinoglutaric acid (JS-2-13-P1) in 2.8% DMSO, or (S)-(−)-2-methyl-2-phthalimidinoglutaric acid (JS-2-13-P2) in 2.8% DMSO four times a day beginning 72 hours after injection of the tumor cells. Fourteen days after tumor cell inoculation, the lungs were removed from the mice and the surface pulmonary metastases were counted. The results of this experiment showed that the (S) isomer has a greater angiogenesis inhibitory activity than does the (R) isomer.

Example 15

Treatment of Pulmonary Metastasis by Analogs of 2-phthalimidinoglutaric Acid.

B16-BL6 melanoma cells (5×10$^4$) were injected intravenously into the tail veins of C57B 1/6 mice. The mice were given intraperitoneal (i.p.) treatments of one of the following solutions four times a day beginning 72 hours after injection of the tumor cells.

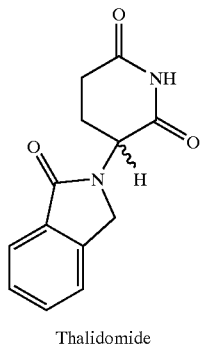

Thalidomide

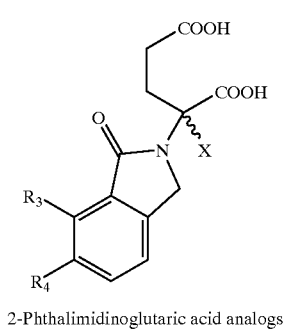

2-Phthalimidinoglutaric acid analogs 1.0 ml of 2.8% DMSO alone (control)
1.0 ml of thalidomide in 2.8% DMSO
1.0 ml of 3'-hydroxy-2-phthalimidinoglutaric acid in 2.8% DMSO (compound 5a)
1.0 ml of 4'-hydroxy-2-phthalimidinoglutaric acid in 2.8% DMSO (compound 5b)
1.0 ml of 2-phthalimlidinoglutaric acid (EM-138) in 2.8% DMSO (compound 5c)
1.0 ml of DL-2-methyl-2-phthalimidinoglutaric acid (racemate) in 2.8% DMSO (compound 7)
1.0 ml of (R)-(+)-2-methyl-2-phthalimidinoglutaric acid (JS-2-13-P1) in 2.8% DMSO (compound 7-R-(+))
1.0 ml of (S)-(−)-2-methyl-2-phthalimidinoglutaric acid (JS-2-13-P2) in 2.8% DMSO (compound 7-S-(−))

A dose of 0.4 mmol/kg was used for each compound tested. Fourteen days after tumor cell inoculation, the lungs were removed from the mice and the surface pulmonary metastases were counted. The results of this experiment are provided in the following table.

TABLE 1

| Compound | X | $R_3$ | $R_4$ | T/C[a] |
|---|---|---|---|---|
| Thalidomide | — | — | — | 0.9 |
| 5a | H | OH | H | 0.95 |
| 5b | H | H | OH | 0.9 |
| 5c (EM-138) | H | H | H | 0.2 |
| 7 | $CH_3$ | H | H | 0.25 |
| 7-R-(+) | $CH_3$ | H | H | 0.7 |
| 7-S-(−) | $CH_3$ | H | H | 0.15 |

[a]T/C is defined as the ratio of lung metastases of treated (T) animals vs. non-treated or control (C) animals.

This experiment was repeated at varying doses. The data in the following table represent the average values for three runs of the experiment.

TABLE 2

| Compound | X | $R_3$ | $R_4$ | $IC_{50}$ (mmol/kg) |
|---|---|---|---|---|
| Thalidomide | — | — | — | 3.2[a] |
| 5c (EM-138) | H | H | H | 0.2[a] |
| 7 | $CH_3$ | H | H | 0.2[a] |
| 7-R-(+) | $CH_3$ | H | H | No activity[b] |
| 7-S-(−) | $CH_3$ | H | H | 0.1[a] |

$IC_{50}$ = 50% inhibition of surface metastasis
[a]These data represent the average of three experiments.
[b]This enantiomer showed no appreciable activity up 0.8 mmol/kg and was only tested once at each dose.

These data show that EM-138 and 2-methyl-EM-138 have similar anti-tumor activity and are both have considerably greater inhibitory activity than thalidomide. These data also show 2-methyl-EM-138's activity is attributable to the (S) isomer, with the (R) isomer showing little or no activity. Also, it appears that analogs of EM-138 containing hydroxyl groups on the benzene ring of the phthalimidino group in the absence of the 2-methyl group show little or no anti-tumor activity at the tested doses.

It should be understood, of course, that the foregoing relates only to preferred embodiments of the present invention and that numerous modifications or alterations may be made therein without departing from the spirit and the scope of the invention as set forth in the appended claims.

What is claimed is:

1. A process for preparing 2-methyl-2-phthalimidinoglutaric acid comprising the steps of
    a) reacting 2-methylglutamic acid, phthalic anhydride, and an amine in an anhydrous solvent;
    b) recovering the 2-methyl-N-phthaloylglutamic acid intermediate;
    c) dissolving the 2-methyl-N-phthaloylglutamic acid intermediate in acid followed by the addition of zinc dust;
    d) heating the mixture formed in c) under reflux in an inert atmosphere; and
    e) recovering, and optionally purifying, the resulting 2-methyl-2-phthalimidinoglutaric acid.

2. The process of claim 1, wherein the amine is selected from the group consisting of triethyl amine, diethyl amine, and pyridine.

3. The process of claim 1, wherein the acid is glacial acetic acid.

4. A process for the separation of the (S) and (R) enantiomers of DL-2-methyl-2-phthalimidinoglutaric acid comprising the steps of
    a) placing a solution of DL-2-methyl-2-phthalimidinoglutaric acid on a chiral HPLC column; and
    b) separately eluting R-(+)-2-methyl-2-phthalimidinoglutaric acid and S-(−)-2-methyl-2-phthalimidinoglutaric acid.

5. The process of claim 4, wherein (R)-(+)-2-methyl-2-phthalimidinoglutaric acid and (S)-(−)-2-methyl-2-phthalimidino-glutaric acid are separately eluted from the HPLC column with a solvent mixture comprising $CH_3CN$/$MeOH$/$H_2O$/HOAc in a molar ratio of 1:1:5:0.1.

6. A process for the separation of the (S) and (R) enantiomers of DL-2-methyl-2-phthalimidinoglutaric acid comprising the steps of
    a) forming a diester of DL-2-methyl-2-phthalimidinoglutaric acid;
    b) separating the diester enantiomers with an enantiomerically-specific hydrolysis agent;
    c) separating the hydrolyzed products on a silica gel column; and
    d) completely hydrolyzing the individual enantiomers to form R-(+)-2-methyl-2-phthalimidino-glutaric acid and S-(−)-2-methyl-2-phthalimidinoglutaric acid.

7. The process of claim 6, wherein the enantiomerically-specific hydrolysis agent in step (b) is crosslinked Bacillus licheniformis Subtilisin microcrystals ChiroCLEC™-BL.

8. The process of claim 6, wherein the individual enantiomers are completely hydrolyzed by treating the partially hydrolyzed intermediates formed in step (c) with a 1:1 mixture of glacial acetic acid and concentrated hydrochloric acid.

9. A pharmaceutical composition comprising a pharmaceutically acceptable carrier and a stereoisomer of a compound having the formula

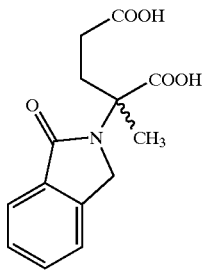

wherein the stereoisomer consists essentially of S-(−)-2-methyl-2-phthalimidinoglutaric acid.

10. The composition of claim 9, wherein the composition is in the form of tablets, pills, capsules, suppositories, sachets, granules, powders, creams, lotions, ointments, patches, liquid solutions, suspensions, dispersions, emulsions, syrups, liposomes, microparticles, and microcapsules.

11. A method of inhibiting undesired angiogenesis in a human or animal comprising administering to the human or animal with undesired angiogenesis an angiogenesis inhibiting amount of a stereoisomer of a compound having the formula

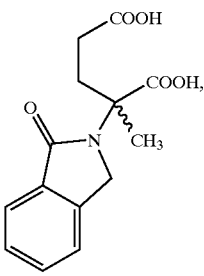

wherein the stereoisomer consists essentially of S-(−)-2-methyl-2-phthalimidinoglutaric acid.

12. The method of claim 11, wherein the administration is oral, parenteral, rectal, vaginal, topical, transdermal, intravenous, intramuscular, intraperatoneal, or subcutaneous.

13. The method of claim 11, wherein the effective amount is from approximately 100 mg/kg/day to approximately 2000 mg/kg/day.

14. The method of claim 11, wherein the undesired angiogenesis occurs in a disease selected from the group consisting of diabetic retinopathy, retinopathy of prematurity, corneal graph rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sjogren's syndrome, acne rosacea, phylectenulosis, syphilis, Micobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus erythematosis, polyarteritis, Wegener's sarcoidosis, scleritis, Stevens-Johnson disease, radial keratotomy, macular degeneration, sickle cell anemia, sarcoid, pseudoxanthoma elasticum, Paget's disease, vein occlusion, artery occlusion, carotid obstructive disease, chronic uveitis, chronic vitritis, Lyme's disease, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, post-laser complications, rubeosis, abnormal proliferation of fibrovascular or fibrous tissue, proliferative vitreoretinopathy, Bartonellosis, hemangiomas, Osler-Weber-Rendu disease, solid tumors, blood-borne tumors, acquired immune deficiency syndrome, ocular neovascular disease, age-related macular degeneration, osteoarthritis, gliomas, diseases caused by chronic inflammation, Crohn's disease, ulceritive colitis, tumors of rhabdomyosarcoma, tumors of retinblastoma, tumors of Ewing's sarcoma, tumors of neuroblastoma, tumors of osteosarcoma, leukemia, psoriasis, atherosclerosis, acoustic neuroma, neurofibroma, trachoma, pyogenic granulomas, and pemphigoid.

15. The method of claim 14, wherein the administration is oral, parenteral, rectal, vaginal, topical, transdermal, intravenous, intramuscular, intraperatoneal, or subcutaneous.

16. The method of claim 14, wherein the effective amount is from approximately 100 mg/kg/day to approximately 2000 mg/kg/day.

17. A method of treating cancer in a human or animal comprising administering to the human or animal having cancer a cancer treatment effective amount of a stereoisomer of a compound having the formula

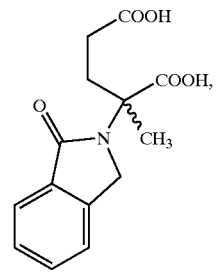

wherein the stereoisomer consists essentially of S-(−)-2-methyl-2-phthalimidinoglutaric acid.

18. The method of claim 17, wherein the administration is oral, parenteral, rectal, vaginal, topical, transdermal, intravenous, intramuscular, intraperatoneal, or subcutaneous.

19. The method of claim 17, wherein the effective amount is from approximately 100 mg/kg/day to approximately 2000 mg/kg/day.

* * * * *